United States Patent
Powell et al.

(10) Patent No.: US 10,400,277 B2
(45) Date of Patent: Sep. 3, 2019

(54) DNA MUTATION DETECTION EMPLOYING ENRICHMENT OF MUTANT POLYNUCLEOTIDE SEQUENCES AND MINIMALLY INVASIVE SAMPLING

(71) Applicants: Michael J Powell, Alamo, CA (US); Aiguo Zhang, San Ramon, CA (US)

(72) Inventors: Michael J Powell, Alamo, CA (US); Aiguo Zhang, San Ramon, CA (US)

(73) Assignee: DIACARTA LTD, George Town (KY)

( * ) Notice: Subject to any disclaimer, the term of this patent is extended or adjusted under 35 U.S.C. 154(b) by 0 days.

(21) Appl. No.: 14/822,874

(22) Filed: Aug. 10, 2015

(65) Prior Publication Data

US 2016/0194691 A1 Jul. 7, 2016

Related U.S. Application Data

(60) Provisional application No. 62/010,339, filed on Jun. 10, 2014, provisional application No. 62/010,357, filed on Jun. 10, 2014, provisional application No. 62/010,359, filed on Jun. 10, 2014.

(51) Int. Cl.
  *C12P 19/34* (2006.01)
  *C12Q 1/6858* (2018.01)

(52) U.S. Cl.
  CPC .................... *C12Q 1/6858* (2013.01)

(58) Field of Classification Search
  CPC .. C12Q 1/6806; C12Q 1/6827; C12Q 1/6886; C12Q 2600/156
  USPC ....................................... 435/91.2
  See application file for complete search history.

(56) References Cited

U.S. PATENT DOCUMENTS

2013/0005589 A1 * 1/2013 Matsumoto .......... C12Q 1/6858 506/7

FOREIGN PATENT DOCUMENTS

| WO | WO2011093606 | * | 4/2011 |
| WO | WO2013138510 | * | 9/2013 |
| WO | WO 2015068957 | * | 5/2015 |

OTHER PUBLICATIONS

Dabritz et al., British Journal of Cancer, 92: 405-412, 2005.*
Wang et al., Theranostics, 3(6):395-406, May 5, 2013.*
Oh et al., Journal of Molecular Diagnostics 12(4):418-424, Jul. 2010.*
Behn et al., Journal of Pathology 190:69-75, 2000.*
Thiede et al., Nucleic acid research, 24(5):983-984, 1996.*
Oldenburg et al., Journal of Investigative Dermatology, 128:398-402, 2008.*
DiaCarta, Inc. (Molecular Diagnostics); et al http://www.dennisbittnerphd.com/portfolio/Molecular-Disgnostic-Manual.pdf,Park pp. 1-22, Dec. 1, 2013).*

* cited by examiner

*Primary Examiner* — Cynthia B Wilder
(74) *Attorney, Agent, or Firm* — Isaac Angres

(57) ABSTRACT

The invention relates to a method for enriching a target polynucleotide sequence containing a genetic variation said method comprising: (a) providing two primers targeted to said target polynucleotide sequence; (b) providing a target specific xenonucleic acid clamp oligomer specific for a wildtype polynucleotide sequence; (c) generating multiple amplicons using PCR under specific temperature cycling conditions; and (d) detecting said amplicons.

9 Claims, 6 Drawing Sheets

Specification includes a Sequence Listing.

Figure 1. The modified DNA oligo probe binds—or clamps—to wild-type DNA and blocks further wild-type DNA amplification. This probe, or XNA "clamp" does not bind to mutated DNA, allowing it to be amplified and detected.

Figure 4

FLUOROPHORE SPECTRAL DATA AND QUENCHER SELECTION GUIDE

| Fluorophore | Color | Absorbance max (nm) | Emission max (nm) | Quencher Guide |
|---|---|---|---|---|
| 6-FAM (Fluorescein) | Green | 494 | 525 | BHQ-1/Dabcyl |
| TET | Orange | 521 | 536 | BHQ-1/Dabcyl |
| HEX | Pink | 535 | 556 | BHQ-1/Dabcyl |
| Cy 3 | Red | 552 | 570 | BHQ-2 |
| Cy 3.5 | Purple | 588 | 604 | BHQ-2 |
| Cy 5 | Violet | 646 | 667 | BHQ-3 |
| Cy 5.5 | Blue | 683 | 707 | BHQ-3 |
| Cy 7 | Near IR | 743 | 767 | BHQ-3 |
| Tamra | Rose | 565 | 580 | BHQ-2 |
| ROX | Purple | 587 | 607 | BHQ-2 |
| JOE | Mustard | 528 | 554 | BHQ-1/Dabcyl |
| Texas Red-X | Red | 583 | 603 | BHQ-2 |
| Cascade Blue | Blue | 396 | 410 | BHQ-1/Dabcyl |
| Marina Blue | Blue | 362 | 459 | BHQ-1/Dabcyl |

SEQUENCE LISTING

<160> NUMBER OF SEQ ID NOS: 206

<210> SEQ ID NO 1
<211> LENGTH: 13
<212> TYPE: DNA
<213> ORGANISM: Artificial
<220> FEATURE:
<223> OTHER INFORMATION: synthetic

<400> SEQUENCE: 1
agctgctggc gta                                                          13

<210> SEQ ID NO 2
<211> LENGTH: 13
<212> TYPE: DNA
<213> ORGANISM: Artificial
<220> FEATURE:
<223> OTHER INFORMATION: synthetic

<400> SEQUENCE: 2
agctcgtggc gta                                                          13

<210> SEQ ID NO 3

```
<211> LENGTH: 13
<212> TYPE: DNA
<213> ORGANISM: Artificial
<220> FEATURE:
<223> OTHER INFORMATION: synthetic

<400> SEQUENCE: 3
agctgatggc gta                                                          13

<210> SEQ ID NO 4
<211> LENGTH: 13
<212> TYPE: DNA
<213> ORGANISM: Artificial
<220> FEATURE:
<223> OTHER INFORMATION: synthetic

<400> SEQUENCE: 4
agcttgtggc gta                                                          13

<210> SEQ ID NO 5
<211> LENGTH: 13
<212> TYPE: DNA
<213> ORGANISM: Artificial
<220> FEATURE:
<223> OTHER INFORMATION: synthetic

<400> SEQUENCE: 5
gagctattgg cgt                                                          13

<210> SEQ ID NO 6
<211> LENGTH: 13
<212> TYPE: DNA
<213> ORGANISM: Artificial
<220> FEATURE:
<223> OTHER INFORMATION: synthetic

<400> SEQUENCE: 6
gagctcttgg cgt                                                          13

<210> SEQ ID NO 7
<211> LENGTH: 13
<212> TYPE: DNA
<213> ORGANISM: Artificial
<220> FEATURE:
<223> OTHER INFORMATION: synthetic

<400> SEQUENCE: 7
agctagtggc gta                                                          13

<210> SEQ ID NO 8
<211> LENGTH: 13
<212> TYPE: DNA
<213> ORGANISM: Artificial
<220> FEATURE:
<223> OTHER INFORMATION: synthetic

<400> SEQUENCE: 8
agctgttggc gta                                                          13

<210> SEQ ID NO 9
<211> LENGTH: 13
<212> TYPE: DNA
<213> ORGANISM: Artificial
<220> FEATURE:
<223> OTHER INFORMATION: synthetic

<400> SEQUENCE: 9
```
tggttgcgta ggc                                                      13

<210> SEQ ID NO 10
<211> LENGTH: 13
<212> TYPE: DNA
<213> ORGANISM: Artificial
<220> FEATURE:
<223> OTHER INFORMATION: synthetic

<400> SEQUENCE: 10
tggtgacgta ggc                                                      13

<210> SEQ ID NO 11
<211> LENGTH: 13
<212> TYPE: DNA
<213> ORGANISM: Artificial
<220> FEATURE:
<223> OTHER INFORMATION: synthetic

<400> SEQUENCE: 11
tggtgccgta ggc                                                      13

<210> SEQ ID NO 12
<211> LENGTH: 13
<212> TYPE: DNA
<213> ORGANISM: Artificial
<220> FEATURE:
<223> OTHER INFORMATION: synthetic

<400> SEQUENCE: 12
tggtgtcgta ggc                                                      13

<210> SEQ ID NO 13
<211> LENGTH: 13
<212> TYPE: DNA
<213> ORGANISM: Artificial
<220> FEATURE:
<223> OTHER INFORMATION: synthetic

<400> SEQUENCE: 13
tggtagcgta ggc                                                      13

<210> SEQ ID NO 14
<211> LENGTH: 13
<212> TYPE: DNA
<213> ORGANISM: Artificial
<220> FEATURE:
<223> OTHER INFORMATION: synthetic

<400> SEQUENCE: 14
tggtcgcgta ggc                                                      13

<210> SEQ ID NO 15
<211> LENGTH: 13
<212> TYPE: DNA
<213> ORGANISM: Artificial
<220> FEATURE:
<223> OTHER INFORMATION: synthetic

<400> SEQUENCE: 15
ggagacggtc tgg                                                      13

<210> SEQ ID NO 16
<211> LENGTH: 13
<212> TYPE: DNA

```
<213> ORGANISM: Artificial
<220> FEATURE:
<223> OTHER INFORMATION: synthetic

<400> SEQUENCE: 16
ggagacgctc tgg                                                        13

<210> SEQ ID NO 17
<211> LENGTH: 13
<212> TYPE: DNA
<213> ORGANISM: Artificial
<220> FEATURE:
<223> OTHER INFORMATION: synthetic

<400> SEQUENCE: 17
ctggtggcgt agg                                                        13

<210> SEQ ID NO 18
<211> LENGTH: 13
<212> TYPE: DNA
<213> ORGANISM: Artificial
<220> FEATURE:
<223> OTHER INFORMATION: synthetic

<400> SEQUENCE: 18
aaggcctgct gaa                                                        13

<210> SEQ ID NO 19
<211> LENGTH: 24
<212> TYPE: DNA
<213> ORGANISM: Artificial
<220> FEATURE:
<223> OTHER INFORMATION: synthetic

<400> SEQUENCE: 19
gtactggtgg agtatttgat agtg                                            24

<210> SEQ ID NO 20
<211> LENGTH: 23
<212> TYPE: DNA
<213> ORGANISM: Artificial
<220> FEATURE:
<223> OTHER INFORMATION: synthetic

<400> SEQUENCE: 20
atcgtcaagg cactcttgcc tac                                             23

<210> SEQ ID NO 21
<211> LENGTH: 27
<212> TYPE: DNA
<213> ORGANISM: artificial
<220> FEATURE:
<223> OTHER INFORMATION: synthetic

<400> SEQUENCE: 21
cgaaagaccc tagccttaga taaaact                                         27

<210> SEQ ID NO 22
<211> LENGTH: 25
<212> TYPE: DNA
<213> ORGANISM: artificial
<220> FEATURE:
<223> OTHER INFORMATION: synthetic

<400> SEQUENCE: 22
attgtgtgga agatccaatc cattt                                           25
```

<210> SEQ ID NO 23
<211> LENGTH: 32
<212> TYPE: DNA
<213> ORGANISM: artificial
<220> FEATURE:
<223> OTHER INFORMATION: synthetic

<400> SEQUENCE: 23
acgttggatg tgtaccatac ctgtctggtc tt                                      32

<210> SEQ ID NO 24
<211> LENGTH: 48
<212> TYPE: DNA
<213> ORGANISM: artificial
<220> FEATURE:
<223> OTHER INFORMATION: synthetic

<400> SEQUENCE: 24
gttttcccag tcacgacacg ttggatgcag ccaggaacgt actggtga                     48

<210> SEQ ID NO 25
<211> LENGTH: 23
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(23)
<223> OTHER INFORMATION: Biotin modified
<220> FEATURE:
<221> NAME/KEY: modified_base
<222> LOCATION: (1)..(23)

<400> SEQUENCE: 25
ctccagatct cagtaaggta cgg                                                23

<210> SEQ ID NO 26
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: Biotin modified

<400> SEQUENCE: 26
tgagggagat ccgacaatac ag                                                 22

<210> SEQ ID NO 27
<211> LENGTH: 31
<212> TYPE: DNA
<213> ORGANISM: artificial
<220> FEATURE:
<223> OTHER INFORMATION: synthetic

<400> SEQUENCE: 27
acagtaaaaa taggtgattt tggtctagct a                                       31

<210> SEQ ID NO 28
<211> LENGTH: 58
<212> TYPE: DNA
<213> ORGANISM: artificial
<220> FEATURE:
<223> OTHER INFORMATION: synthetic

<400> SEQUENCE: 28
gttttcccag tcacgacacg ttggatgaca gtaaaaatag gtgatttgg tctagcta    58

<210> SEQ ID NO 29
<211> LENGTH: 24
<212> TYPE: DNA
<213> ORGANISM: artificial
<220> FEATURE:
<223> OTHER INFORMATION: synthetic

<400> SEQUENCE: 29
catccacaaa atggatccag acaa    24

<210> SEQ ID NO 30
<211> LENGTH: 51
<212> TYPE: DNA
<213> ORGANISM: artificial
<220> FEATURE:
<223> OTHER INFORMATION: synthetic

<400> SEQUENCE: 30
caggaaacag ctatgacacg ttggatgcat ccacaaaatg gatccagaca a    51

<210> SEQ ID NO 31
<211> LENGTH: 23
<212> TYPE: DNA
<213> ORGANISM: artificial
<220> FEATURE:
<223> OTHER INFORMATION: synthetic

<400> SEQUENCE: 31
ctccagatct cagtaaggta cgg    23

<210> SEQ ID NO 32
<211> LENGTH: 21
<212> TYPE: DNA
<213> ORGANISM: artificial
<220> FEATURE:
<223> OTHER INFORMATION: synthetic

<400> SEQUENCE: 32
gggaaagagt ggtctctcat c    21

<210> SEQ ID NO 33
<211> LENGTH: 28
<212> TYPE: DNA
<213> ORGANISM: artificial
<220> FEATURE:
<223> OTHER INFORMATION: synthetic

<400> SEQUENCE: 33
acgttggatg tccaccgtgc agctcatc    28

<210> SEQ ID NO 34
<211> LENGTH: 41
<212> TYPE: DNA
<213> ORGANISM: artificial
<220> FEATURE:
<223> OTHER INFORMATION: synthetic

<400> SEQUENCE: 34
gttttcccag tcacgacacg ttggatgtcc accgtgcagc t    41

<210> SEQ ID NO 35

<211> LENGTH: 30
<212> TYPE: DNA
<213> ORGANISM: artificial
<220> FEATURE:
<223> OTHER INFORMATION: synthetic

<400> SEQUENCE: 35
acgttggatg gtctttgtgt tcccggacat                              30

<210> SEQ ID NO 36
<211> LENGTH: 41
<212> TYPE: DNA
<213> ORGANISM: artificial
<220> FEATURE:
<223> OTHER INFORMATION: synthetic

<400> SEQUENCE: 36
caggaaacag ctatgacacg ttggatggtc tttgtgttcc c                 41

<210> SEQ ID NO 37
<211> LENGTH: 53
<212> TYPE: DNA
<213> ORGANISM: artificial
<220> FEATURE:
<223> OTHER INFORMATION: synthetic

<400> SEQUENCE: 37
gttttcccag tcacgacacg ttggatgctc tctgtcatag ggactctgga tcc    53

<210> SEQ ID NO 38
<211> LENGTH: 26
<212> TYPE: DNA
<213> ORGANISM: artificial
<220> FEATURE:
<223> OTHER INFORMATION: synthetic

<400> SEQUENCE: 38
ctctctgtca tagggactct ggatcc                                  26

<210> SEQ ID NO 39
<211> LENGTH: 24
<212> TYPE: DNA
<213> ORGANISM: artificial
<220> FEATURE:
<223> OTHER INFORMATION: synthetic

<400> SEQUENCE: 39
agcaaagcag aaactcacat cgag                                    24

<210> SEQ ID NO 40
<211> LENGTH: 51
<212> TYPE: DNA
<213> ORGANISM: artificial
<220> FEATURE:
<223> OTHER INFORMATION: synthetic

<400> SEQUENCE: 40
caggaaacag ctatgacacg ttggatgagc aaagcagaaa ctcacatcga g      51

<210> SEQ ID NO 41
<211> LENGTH: 49
<212> TYPE: DNA
<213> ORGANISM: artificial
<220> FEATURE:
<223> OTHER INFORMATION: synthetic

<400> SEQUENCE: 41

-continued

```
gttttcccag tcacgacacg ttggatggct cccaaccaag ctctcttga        49
```

<210> SEQ ID NO 42
<211> LENGTH: 22
<212> TYPE: DNA
<213> ORGANISM: artificial
<220> FEATURE:
<223> OTHER INFORMATION: synthetic

<400> SEQUENCE: 42

```
gctcccaacc aagctctctt ga        22
```

<210> SEQ ID NO 43
<211> LENGTH: 25
<212> TYPE: DNA
<213> ORGANISM: artificial
<220> FEATURE:
<223> OTHER INFORMATION: synthetic

<400> SEQUENCE: 43

```
ctgtgccagg gaccttacct tatac        25
```

<210> SEQ ID NO 44
<211> LENGTH: 52
<212> TYPE: DNA
<213> ORGANISM: artificial
<220> FEATURE:
<223> OTHER INFORMATION: synthetic

<400> SEQUENCE: 44

```
caggaaacag ctatgacacg ttggatgctg tgccagggac cttaccttat ac        52
```

<210> SEQ ID NO 45
<211> LENGTH: 23
<212> TYPE: DNA
<213> ORGANISM: artificial
<220> FEATURE:
<223> OTHER INFORMATION: synthetic

<400> SEQUENCE: 45

```
tttgccaagg cacgagtaac aag        23
```

<210> SEQ ID NO 46
<211> LENGTH: 23
<212> TYPE: DNA
<213> ORGANISM: artificial
<220> FEATURE:
<223> OTHER INFORMATION: synthetic

<400> SEQUENCE: 46

```
cccaaggacc acctcacagt tat        23
```

<210> SEQ ID NO 47
<211> LENGTH: 26
<212> TYPE: DNA
<213> ORGANISM: artificial
<220> FEATURE:
<223> OTHER INFORMATION: synthetic

<400> SEQUENCE: 47

```
ttaactgcag atgcacatca ttacct        26
```

<210> SEQ ID NO 48
<211> LENGTH: 23
<212> TYPE: DNA

```
<213> ORGANISM: artificial
<220> FEATURE:
<223> OTHER INFORMATION: synthetic

<400> SEQUENCE: 48
ggactctgaa gatgtaccta tgg                                          23

<210> SEQ ID NO 49
<211> LENGTH: 50
<212> TYPE: DNA
<213> ORGANISM: artificial
<220> FEATURE:
<223> OTHER INFORMATION: synthetic

<400> SEQUENCE: 49
gttttcccag tcacgacacg ttggatggga ctctgaagat gtacctatgg             50

<210> SEQ ID NO 50
<211> LENGTH: 20
<212> TYPE: DNA
<213> ORGANISM: artificial
<220> FEATURE:
<223> OTHER INFORMATION: synthetic

<400> SEQUENCE: 50
gctaagtcct gagcctgttt                                              20

<210> SEQ ID NO 51
<211> LENGTH: 47
<212> TYPE: DNA
<213> ORGANISM: artificial
<220> FEATURE:
<223> OTHER INFORMATION: synthetic

<400> SEQUENCE: 51
caggaaacag ctatgacacg ttggatggct aagtcctgag cctgttt                47

<210> SEQ ID NO 52
<211> LENGTH: 20
<212> TYPE: DNA
<213> ORGANISM: artificial
<220> FEATURE:
<223> OTHER INFORMATION: synthetic

<400> SEQUENCE: 52
acacaaaaca ggctcaggac                                              20

<210> SEQ ID NO 53
<211> LENGTH: 47
<212> TYPE: DNA
<213> ORGANISM: artificial
<220> FEATURE:
<223> OTHER INFORMATION: synthetic

<400> SEQUENCE: 53
gttttcccag tcacgacacg ttggatgaca caaaacaggc tcaggac                47

<210> SEQ ID NO 54
<211> LENGTH: 25
<212> TYPE: DNA
<213> ORGANISM: artificial
<220> FEATURE:
<223> OTHER INFORMATION: synthetic

<400> SEQUENCE: 54
cagtgttact tacctgtctt gtctt                                        25
```

<210> SEQ ID NO 55
<211> LENGTH: 52
<212> TYPE: DNA
<213> ORGANISM: artificial
<220> FEATURE:
<223> OTHER INFORMATION: synthetic

<400> SEQUENCE: 55
caggaaacag ctatgacacg ttggatgcag tgttacttac ctgtcttgtc tt    52

<210> SEQ ID NO 56
<211> LENGTH: 21
<212> TYPE: DNA
<213> ORGANISM: artificial
<220> FEATURE:
<223> OTHER INFORMATION: synthetic

<400> SEQUENCE: 56
aaggcctgct gaaaatgact g    21

<210> SEQ ID NO 57
<211> LENGTH: 48
<212> TYPE: DNA
<213> ORGANISM: artificial
<220> FEATURE:
<223> OTHER INFORMATION: synthetic

<400> SEQUENCE: 57
gttttcccag tcacgacacg ttggatgaag gcctgctgaa aatgactg    48

<210> SEQ ID NO 58
<211> LENGTH: 48
<212> TYPE: DNA
<213> ORGANISM: artificial
<220> FEATURE:
<223> OTHER INFORMATION: synthetic

<400> SEQUENCE: 58
caggaaacag ctatgacacg ttggatgtca aggcactctt gcctacgc    48

<210> SEQ ID NO 59
<211> LENGTH: 22
<212> TYPE: DNA
<213> ORGANISM: artificial
<220> FEATURE:
<223> OTHER INFORMATION: synthetic

<400> SEQUENCE: 59
acttgtggta gttggagctg gt    22

<210> SEQ ID NO 60
<211> LENGTH: 49
<212> TYPE: DNA
<213> ORGANISM: artificial
<220> FEATURE:
<223> OTHER INFORMATION: synthetic

<400> SEQUENCE: 60
gttttcccag tcacgacacg ttggatgact tgtggtagtt ggagctggt    49

<210> SEQ ID NO 61
<211> LENGTH: 25
<212> TYPE: DNA
<213> ORGANISM: artificial
<220> FEATURE:

<223> OTHER INFORMATION: synthetic

<400> SEQUENCE: 61
tcatgaaaat ggtcagagaa acctt                                    25

<210> SEQ ID NO 62
<211> LENGTH: 49
<212> TYPE: DNA
<213> ORGANISM: artificial
<220> FEATURE:
<223> OTHER INFORMATION: synthetic

<400> SEQUENCE: 62
caggaaacag ctatgacacg ttggatgact tgtggtagtt ggagctggt          49

<210> SEQ ID NO 63
<211> LENGTH: 23
<212> TYPE: DNA
<213> ORGANISM: artificial
<220> FEATURE:
<223> OTHER INFORMATION: synthetic

<400> SEQUENCE: 63
attgcactgt actcctcttg acc                                      23

<210> SEQ ID NO 64
<211> LENGTH: 50
<212> TYPE: DNA
<213> ORGANISM: artificial
<220> FEATURE:
<223> OTHER INFORMATION: synthetic

<400> SEQUENCE: 64
caggaaacag ctatgacacg ttggatgatt gcactgtact cctcttgacc         50

<210> SEQ ID NO 65
<211> LENGTH: 27
<212> TYPE: DNA
<213> ORGANISM: artificial
<220> FEATURE:
<223> OTHER INFORMATION: synthetic

<400> SEQUENCE: 65
ctcttggata ttctcgacac agcaggt                                  27

<210> SEQ ID NO 66
<211> LENGTH: 54
<212> TYPE: DNA
<213> ORGANISM: artificial
<220> FEATURE:
<223> OTHER INFORMATION: synthetic

<400> SEQUENCE: 66
gttttcccag tcacgacacg ttggatgctc ttggatattc tcgacacagc aggt    54

<210> SEQ ID NO 67
<211> LENGTH: 20
<212> TYPE: DNA
<213> ORGANISM: artificial
<220> FEATURE:
<223> OTHER INFORMATION: synthetic

<400> SEQUENCE: 67
ccagactgtg tttctccctt                                          20

<210> SEQ ID NO 68
<211> LENGTH: 47
<212> TYPE: DNA
<213> ORGANISM: artificial
<220> FEATURE:
<223> OTHER INFORMATION: synthetic

<400> SEQUENCE: 68
gttttcccag tcacgacacg ttggatgcca gactgtgttt ctccctt        47

<210> SEQ ID NO 69
<211> LENGTH: 22
<212> TYPE: DNA
<213> ORGANISM: artificial
<220> FEATURE:
<223> OTHER INFORMATION: synthetic

<400> SEQUENCE: 69
tgagggagat ccgacaatac ag        22

<210> SEQ ID NO 70
<211> LENGTH: 25
<212> TYPE: DNA
<213> ORGANISM: artificial
<220> FEATURE:
<223> OTHER INFORMATION: synthetic

<400> SEQUENCE: 70
tctgccaaaa ttaatgtgct gaact        25

<210> SEQ ID NO 71
<211> LENGTH: 18
<212> TYPE: DNA
<213> ORGANISM: artificial
<220> FEATURE:
<223> OTHER INFORMATION: synthetic

<400> SEQUENCE: 71
ttctcttccg cacccagc        18

<210> SEQ ID NO 72
<211> LENGTH: 45
<212> TYPE: DNA
<213> ORGANISM: artificial
<220> FEATURE:
<223> OTHER INFORMATION: synthetic

<400> SEQUENCE: 72
caggaaacag ctatgacacg ttggatgttc tcttccgcac ccagc        45

<210> SEQ ID NO 73
<211> LENGTH: 51
<212> TYPE: DNA
<213> ORGANISM: artificial
<220> FEATURE:
<223> OTHER INFORMATION: synthetic

<400> SEQUENCE: 73
gttttcccag tcacgacacg ttggatgtga aaacaccgca gcatgtcaag a        51

<210> SEQ ID NO 74
<211> LENGTH: 24
<212> TYPE: DNA
<213> ORGANISM: artificial
<220> FEATURE:
<223> OTHER INFORMATION: synthetic

<400> SEQUENCE: 74
tgaaaacacc gcagcatgtc aaga                                          24

<210> SEQ ID NO 75
<211> LENGTH: 24
<212> TYPE: DNA
<213> ORGANISM: artificial
<220> FEATURE:
<223> OTHER INFORMATION: synthetic

<400> SEQUENCE: 75
ccttactttg cctccttctg catg                                          24

<210> SEQ ID NO 76
<211> LENGTH: 51
<212> TYPE: DNA
<213> ORGANISM: artificial
<220> FEATURE:
<223> OTHER INFORMATION: synthetic

<400> SEQUENCE: 76
caggaaacag ctatgacacg ttggatgcct tactttgcct ccttctgcat g            51

<210> SEQ ID NO 77
<211> LENGTH: 26
<212> TYPE: DNA
<213> ORGANISM: artificial
<220> FEATURE:
<223> OTHER INFORMATION: synthetic

<400> SEQUENCE: 77
tggtgggatc atattcatct acaaag                                        26

<210> SEQ ID NO 78
<211> LENGTH: 26
<212> TYPE: DNA
<213> ORGANISM: artificial
<220> FEATURE:
<223> OTHER INFORMATION: synthetic

<400> SEQUENCE: 78
tggtgggatc atattcatct acaaag                                        26

<210> SEQ ID NO 79
<211> LENGTH: 53
<212> TYPE: DNA
<213> ORGANISM: artificial
<220> FEATURE:
<223> OTHER INFORMATION: synthetic

<400> SEQUENCE: 79
caggaaacag ctatgacacg ttggatgtgg tgggatcata ttcatctaca aag          53

<210> SEQ ID NO 80
<211> LENGTH: 27
<212> TYPE: DNA
<213> ORGANISM: artificial
<220> FEATURE:
<223> OTHER INFORMATION: synthetic

<400> SEQUENCE: 80
agtaaaagac tcggatgatg tacctat                                       27

<210> SEQ ID NO 81
<211> LENGTH: 32

```
<212> TYPE: DNA
<213> ORGANISM: artificial
<220> FEATURE:
<223> OTHER INFORMATION: synthetic

<400> SEQUENCE: 81
acgttggatg acctatggtg ctagtgggaa ac                          32

<210> SEQ ID NO 82
<211> LENGTH: 30
<212> TYPE: DNA
<213> ORGANISM: artificial
<220> FEATURE:
<223> OTHER INFORMATION: synthetic

<400> SEQUENCE: 82
acgttggatg tcccgttttt agggagcaga                             30

<210> SEQ ID NO 83
<211> LENGTH: 20
<212> TYPE: DNA
<213> ORGANISM: artificial
<220> FEATURE:
<223> OTHER INFORMATION: synthetic

<400> SEQUENCE: 83
cccgttttta gggagcagat                                        20

<210> SEQ ID NO 84
<211> LENGTH: 20
<212> TYPE: DNA
<213> ORGANISM: artificial
<220> FEATURE:
<223> OTHER INFORMATION: synthetic

<400> SEQUENCE: 84
cagttcgtgg gcttgttttg                                        20

<210> SEQ ID NO 85
<211> LENGTH: 20
<212> TYPE: DNA
<213> ORGANISM: artificial
<220> FEATURE:
<223> OTHER INFORMATION: synthetic

<400> SEQUENCE: 85
cttgcacaaa tgctgaaagc                                        20

<210> SEQ ID NO 86
<211> LENGTH: 21
<212> TYPE: DNA
<213> ORGANISM: artificial
<220> FEATURE:
<223> OTHER INFORMATION: synthetic

<400> SEQUENCE: 86
aaactggtgg tggttggagc a                                      21

<210> SEQ ID NO 87
<211> LENGTH: 48
<212> TYPE: DNA
<213> ORGANISM: artificial
<220> FEATURE:
<223> OTHER INFORMATION: synthetic

<400> SEQUENCE: 87
```

-continued gttttcccag tcacgacacg ttggatgaaa ctggtggtgg ttggagca        48

<210> SEQ ID NO 88
<211> LENGTH: 19
<212> TYPE: DNA
<213> ORGANISM: artificial
<220> FEATURE:
<223> OTHER INFORMATION: synthetic

<400> SEQUENCE: 88
ggtggtggtt ggagcaggt        19

<210> SEQ ID NO 89
<211> LENGTH: 46
<212> TYPE: DNA
<213> ORGANISM: artificial
<220> FEATURE:
<223> OTHER INFORMATION: synthetic

<400> SEQUENCE: 89
gttttcccag tcacgacacg ttggatgggt ggtggttgga gcaggt        46

<210> SEQ ID NO 90
<211> LENGTH: 22
<212> TYPE: DNA
<213> ORGANISM: artificial
<220> FEATURE:
<223> OTHER INFORMATION: synthetic

<400> SEQUENCE: 90 acaccccag gattcttaca ga        22

<210> SEQ ID NO 91
<211> LENGTH: 49
<212> TYPE: DNA
<213> ORGANISM: artificial
<220> FEATURE:
<223> OTHER INFORMATION: synthetic

<400> SEQUENCE: 91
gttttcccag tcacgacacg ttggatgaca cccccaggat cttacaga        49

<210> SEQ ID NO 92
<211> LENGTH: 23
<212> TYPE: DNA
<213> ORGANISM: artificial
<220> FEATURE:
<223> OTHER INFORMATION: synthetic

<400> SEQUENCE: 92
atggcactgt actcttcttg tcc        23

<210> SEQ ID NO 93
<211> LENGTH: 50
<212> TYPE: DNA
<213> ORGANISM: artificial
<220> FEATURE:
<223> OTHER INFORMATION: synthetic

<400> SEQUENCE: 93
caggaaacag ctatgacacg ttggatgatg gcactgtact cttcttgtcc        50

<210> SEQ ID NO 94
<211> LENGTH: 25
<212> TYPE: DNA
<213> ORGANISM: artificial

<220> FEATURE:
<223> OTHER INFORMATION: synthetic

<400> SEQUENCE: 94
gttggacata ctggatacag ctgga     25

<210> SEQ ID NO 95
<211> LENGTH: 52
<212> TYPE: DNA
<213> ORGANISM: artificial
<220> FEATURE:
<223> OTHER INFORMATION: synthetic

<400> SEQUENCE: 95
gttttcccag tcacgacacg ttggatggtt ggacatactg gatacagctg ga     52

<210> SEQ ID NO 96
<211> LENGTH: 20
<212> TYPE: DNA
<213> ORGANISM: artificial
<220> FEATURE:
<223> OTHER INFORMATION: synthetic

<400> SEQUENCE: 96
ccgcaaatga cttgctatta     20

<210> SEQ ID NO 97
<211> LENGTH: 47
<212> TYPE: DNA
<213> ORGANISM: artificial
<220> FEATURE:
<223> OTHER INFORMATION: synthetic

<400> SEQUENCE: 97
caggaaacag ctatgacacg ttggatgccg caaatgactt gctatta     47

<210> SEQ ID NO 98
<211> LENGTH: 21
<212> TYPE: DNA
<213> ORGANISM: artificial
<220> FEATURE:
<223> OTHER INFORMATION: synthetic

<400> SEQUENCE: 98
acacactggt aagagaaata c     21

<210> SEQ ID NO 99
<211> LENGTH: 18
<212> TYPE: DNA
<213> ORGANISM: artificial
<220> FEATURE:
<223> OTHER INFORMATION: synthetic

<400> SEQUENCE: 99
ctgagtccca tcatcact     18

<210> SEQ ID NO 100
<211> LENGTH: 24
<212> TYPE: DNA
<213> ORGANISM: artificial
<220> FEATURE:
<223> OTHER INFORMATION: synthetic

<400> SEQUENCE: 100
atcgagattt cactgtagct agac     24

<210> SEQ ID NO 101
<211> LENGTH: 19
<212> TYPE: DNA
<213> ORGANISM: artificial
<220> FEATURE:
<223> OTHER INFORMATION: synthetic

<400> SEQUENCE: 101
acttcaggca gcgtcttca                                                   19

<210> SEQ ID NO 102
<211> LENGTH: 19
<212> TYPE: DNA
<213> ORGANISM: artificial
<220> FEATURE:
<223> OTHER INFORMATION: synthetic

<400> SEQUENCE: 102
tgttcagagc acacttcag                                                   19

<210> SEQ ID NO 103
<211> LENGTH: 19
<212> TYPE: DNA
<213> ORGANISM: artificial
<220> FEATURE:
<223> OTHER INFORMATION: synthetic

<400> SEQUENCE: 103
ctggtggttg aatttgctg                                                   19

<210> SEQ ID NO 104
<211> LENGTH: 22
<212> TYPE: DNA
<213> ORGANISM: artificial
<220> FEATURE:
<223> OTHER INFORMATION: synthetic

<400> SEQUENCE: 104
catgagctcc agcaggatga ac                                               22

<210> SEQ ID NO 105
<211> LENGTH: 19
<212> TYPE: DNA
<213> ORGANISM: artificial
<220> FEATURE:
<223> OTHER INFORMATION: synthetic

<400> SEQUENCE: 105
ccgaagtctc caatcttgg                                                   19

<210> SEQ ID NO 106
<211> LENGTH: 19
<212> TYPE: DNA
<213> ORGANISM: artificial
<220> FEATURE:
<223> OTHER INFORMATION: synthetic

<400> SEQUENCE: 106
tagatgtctc gggccatcc                                                   19

<210> SEQ ID NO 107
<211> LENGTH: 15
<212> TYPE: DNA
<213> ORGANISM: artificial
<220> FEATURE:
<223> OTHER INFORMATION: synthetic

```
<400> SEQUENCE: 107
gggacactct aagat                                                    15

<210> SEQ ID NO 108
<211> LENGTH: 18
<212> TYPE: DNA
<213> ORGANISM: artificial
<220> FEATURE:
<223> OTHER INFORMATION: synthetic

<400> SEQUENCE: 108
ttctgtcctg ggattctc                                                 18

<210> SEQ ID NO 109
<211> LENGTH: 18
<212> TYPE: DNA
<213> ORGANISM: artificial
<220> FEATURE:
<223> OTHER INFORMATION: synthetic

<400> SEQUENCE: 109
agattttcca cttgctgt                                                 18

<210> SEQ ID NO 110
<211> LENGTH: 25
<212> TYPE: DNA
<213> ORGANISM: artificial
<220> FEATURE:
<223> OTHER INFORMATION: synthetic

<400> SEQUENCE: 110
ccagatggga cactctaaga ttttc                                         25

<210> SEQ ID NO 111
<211> LENGTH: 23
<212> TYPE: DNA
<213> ORGANISM: artificial
<220> FEATURE:
<223> OTHER INFORMATION: synthetic

<400> SEQUENCE: 111
cctttctgtc ctgggattct ctt                                           23

<210> SEQ ID NO 112
<211> LENGTH: 26
<212> TYPE: DNA
<213> ORGANISM: artificial
<220> FEATURE:
<223> OTHER INFORMATION: synthetic

<400> SEQUENCE: 112
gacagatttt ccacttgctg tgctaa                                        26

<210> SEQ ID NO 113
<211> LENGTH: 22
<212> TYPE: DNA
<213> ORGANISM: artificial
<220> FEATURE:
<223> OTHER INFORMATION: synthetic

<400> SEQUENCE: 113
cataaaggac actgtgaagg cc                                            22

<210> SEQ ID NO 114
```

```
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: D-Lysine modified

<400> SEQUENCE: 114
ggccttcaca gtgtcccttta tg                                          22

<210> SEQ ID NO 115
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: D-Lys Modified

<400> SEQUENCE: 115
cattcttgat gtctctggct ag                                           22

<210> SEQ ID NO 116
<211> LENGTH: 14
<212> TYPE: DNA
<213> ORGANISM: artificial
<220> FEATURE:
<223> OTHER INFORMATION: synthetic

<400> SEQUENCE: 116
gagcccagca cttt                                                    14

<210> SEQ ID NO 117
<211> LENGTH: 19
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(19)
<223> OTHER INFORMATION: D-Lys modified

<400> SEQUENCE: 117
cggagcccag cactttgat                                               19

<210> SEQ ID NO 118
<211> LENGTH: 19
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(19)
<223> OTHER INFORMATION: D-Lys modified

<400> SEQUENCE: 118
cggagcccag cactttgat                                               19

<210> SEQ ID NO 119
<211> LENGTH: 18
<212> TYPE: DNA
<213> ORGANISM: artificial
```

```
<220> FEATURE:
<223> OTHER INFORMATION: synthetic
<220> FEATURE:
<221> NAME/KEY: modified_base
<222> LOCATION: (1)..(18)
<223> OTHER INFORMATION: Amino and carboxamido modified

<400> SEQUENCE: 119
agatgttgct tctcttaa                                                     18

<210> SEQ ID NO 120
<211> LENGTH: 18
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(18)
<223> OTHER INFORMATION: D-Lys modified

<400> SEQUENCE: 120
agatgttgct tctcttaa                                                     18

<210> SEQ ID NO 121
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lys modified

<400> SEQUENCE: 121
cggagatgtt gcttctctta attcc                                             25

<210> SEQ ID NO 122
<211> LENGTH: 16
<212> TYPE: DNA
<213> ORGANISM: artificial
<220> FEATURE:
<223> OTHER INFORMATION: synthetic

<400> SEQUENCE: 122
cagtttggcc agccca                                                       16

<210> SEQ ID NO 123
<211> LENGTH: 16
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(16)
<223> OTHER INFORMATION: D-Lys modified

<400> SEQUENCE: 123
cagtttggcc agccca                                                       16

<210> SEQ ID NO 124
<211> LENGTH: 21
<212> TYPE: DNA
<213> ORGANISM: artificial
<220> FEATURE:
<223> OTHER INFORMATION: synthetic
```

<400> SEQUENCE: 124
tttggccagc ccaaaatctg t                                              21

<210> SEQ ID NO 125
<211> LENGTH: 18
<212> TYPE: DNA
<213> ORGANISM: artificial
<220> FEATURE:
<223> OTHER INFORMATION: synthetic

<400> SEQUENCE: 125
ggccagccca aaatctgt                                                  18

<210> SEQ ID NO 126
<211> LENGTH: 15
<212> TYPE: DNA
<213> ORGANISM: artificial
<220> FEATURE:
<223> OTHER INFORMATION: synthetic

<400> SEQUENCE: 126
acccagcagt ttggc                                                     15

<210> SEQ ID NO 127
<211> LENGTH: 15
<212> TYPE: DNA
<213> ORGANISM: artificial
<220> FEATURE:
<223> OTHER INFORMATION: synthetic

<400> SEQUENCE: 127
acccagcagt ttggc                                                     15

<210> SEQ ID NO 128
<211> LENGTH: 13
<212> TYPE: DNA
<213> ORGANISM: artificial
<220> FEATURE:
<223> OTHER INFORMATION: synthetic

<400> SEQUENCE: 128
gctgcgtgat gag                                                       13

<210> SEQ ID NO 129
<211> LENGTH: 12
<212> TYPE: DNA
<213> ORGANISM: artificial
<220> FEATURE:
<223> OTHER INFORMATION: synthetic

<400> SEQUENCE: 129
gctgcgtgat ga                                                        12

<210> SEQ ID NO 130
<211> LENGTH: 20
<212> TYPE: DNA
<213> ORGANISM: artificial
<220> FEATURE:
<223> OTHER INFORMATION: synthetic

<400> SEQUENCE: 130
agctcatcac gcagctcatg                                                20

<210> SEQ ID NO 131
<211> LENGTH: 22

<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: D-Lys modified

<400> SEQUENCE: 131
cagctcatca cgcagctcat gc                                            22

<210> SEQ ID NO 132
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: D-Lys modified

<400> SEQUENCE: 132
tcatcacgca gctcatgccc tt                                            22

<210> SEQ ID NO 133
<211> LENGTH: 18
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(18)
<223> OTHER INFORMATION: D-Lys modified

<400> SEQUENCE: 133
ctcatcacgc agctcatg                                                 18

<210> SEQ ID NO 134
<211> LENGTH: 14
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(14)
<223> OTHER INFORMATION: D-Lys modified

<400> SEQUENCE: 134
tgagctgcgt gatg                                                     14

<210> SEQ ID NO 135
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lys modified

<400> SEQUENCE: 135
tccacgctgg ccatcacgta                                               20

<210> SEQ ID NO 136

-continued

```
<211> LENGTH: 20
<212> TYPE: DNA
<213> ORGANISM: artificial
<220> FEATURE:
<223> OTHER INFORMATION: synthetic

<400> SEQUENCE: 136
tccacgctgg ccatcacgta                                                 20

<210> SEQ ID NO 137
<211> LENGTH: 14
<212> TYPE: DNA
<213> ORGANISM: artificial
<220> FEATURE:
<223> OTHER INFORMATION: synthetic

<400> SEQUENCE: 137
tgggggttgt ccac                                                       14

<210> SEQ ID NO 138
<211> LENGTH: 15
<212> TYPE: DNA
<213> ORGANISM: artificial
<220> FEATURE:
<223> OTHER INFORMATION: synthetic

<400> SEQUENCE: 138
gcacacgtgg gggtt                                                      15

<210> SEQ ID NO 139
<211> LENGTH: 17
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(17)
<223> OTHER INFORMATION: D-Lys modified

<400> SEQUENCE: 139
acaaccccca cgtgtgc                                                    17

<210> SEQ ID NO 140
<211> LENGTH: 16
<212> TYPE: DNA
<213> ORGANISM: artificial
<220> FEATURE:
<223> OTHER INFORMATION: synthetic

<400> SEQUENCE: 140
ctgagccagg agaaac                                                     16

<210> SEQ ID NO 141
<211> LENGTH: 17
<212> TYPE: DNA
<213> ORGANISM: artificial
<220> FEATURE:
<223> OTHER INFORMATION: synthetic

<400> SEQUENCE: 141
gtaaactgag ccaggag                                                    17

<210> SEQ ID NO 142
<211> LENGTH: 20
<212> TYPE: DNA
<213> ORGANISM: artificial
```

```
<220> FEATURE:
<223> OTHER INFORMATION: synthetic

<400> SEQUENCE: 142
atggcactag taaactgagc                                                  20

<210> SEQ ID NO 143
<211> LENGTH: 21
<212> TYPE: DNA
<213> ORGANISM: artificial
<220> FEATURE:
<223> OTHER INFORMATION: synthetic

<400> SEQUENCE: 143
atccatataa ctgaaagcca a                                                21

<210> SEQ ID NO 144
<211> LENGTH: 23
<212> TYPE: DNA
<213> ORGANISM: artificial
<220> FEATURE:
<223> OTHER INFORMATION: synthetic

<400> SEQUENCE: 144
accacatcat ccatataact gaa                                              23

<210> SEQ ID NO 145
<211> LENGTH: 17
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(17)
<223> OTHER INFORMATION: D-Lys-modified

<400> SEQUENCE: 145
ttgcccacac cgccggc                                                     17

<210> SEQ ID NO 146
<211> LENGTH: 16
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(16)
<223> OTHER INFORMATION: D-Lys-modified

<400> SEQUENCE: 146
tcttgcccac accgcc                                                      16

<210> SEQ ID NO 147
<211> LENGTH: 17
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(17)
<223> OTHER INFORMATION: D-Lys-modified

<400> SEQUENCE: 147
tactcctcct ggccggc                                                     17
```

<210> SEQ ID NO 148
<211> LENGTH: 23
<212> TYPE: DNA
<213> ORGANISM: artificial
<220> FEATURE:
<223> OTHER INFORMATION: synthetic

<400> SEQUENCE: 148
cgtctccaca gacacatact cca                                            23

<210> SEQ ID NO 149
<211> LENGTH: 23
<212> TYPE: DNA
<213> ORGANISM: artificial
<220> FEATURE:
<223> OTHER INFORMATION: synthetic

<400> SEQUENCE: 149
cgtctccaca gacacatact cca                                            23

<210> SEQ ID NO 150
<211> LENGTH: 21
<212> TYPE: DNA
<213> ORGANISM: artificial
<220> FEATURE:
<223> OTHER INFORMATION: synthetic

<400> SEQUENCE: 150
gcctacgcca ccagctccaa c                                              21

<210> SEQ ID NO 151
<211> LENGTH: 21
<212> TYPE: DNA
<213> ORGANISM: artificial
<220> FEATURE:
<223> OTHER INFORMATION: synthetic

<400> SEQUENCE: 151
gcctacgcca ccagctccaa c                                              21

<210> SEQ ID NO 152
<211> LENGTH: 24
<212> TYPE: DNA
<213> ORGANISM: artificial
<220> FEATURE:
<223> OTHER INFORMATION: synthetic

<400> SEQUENCE: 152
ctacgccacc agctccaact acca                                           24

<210> SEQ ID NO 153
<211> LENGTH: 24
<212> TYPE: DNA
<213> ORGANISM: artificial
<220> FEATURE:
<223> OTHER INFORMATION: synthetic

<400> SEQUENCE: 153
ctacgccacc agctccaact acca                                           24

<210> SEQ ID NO 154
<211> LENGTH: 23
<212> TYPE: DNA
<213> ORGANISM: artificial
<220> FEATURE:
<223> OTHER INFORMATION: synthetic

<400> SEQUENCE: 154
tcttgcctac gccaccagct cca                                           23

<210> SEQ ID NO 155
<211> LENGTH: 23
<212> TYPE: DNA
<213> ORGANISM: artificial
<220> FEATURE:
<223> OTHER INFORMATION: synthetic

<400> SEQUENCE: 155
tgtactcctc ttgacctgct gtg                                           23

<210> SEQ ID NO 156
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lys-modified

<400> SEQUENCE: 156
tgtactcctc ttgacctgct gtg                                           23

<210> SEQ ID NO 157
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: Amino and carboxamido modified

<400> SEQUENCE: 157
ggcaaatcac atttatttcc tac                                           23

<210> SEQ ID NO 158
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lys-modified

<400> SEQUENCE: 158
ggcaaatcac atttatttcc tac                                           23

<210> SEQ ID NO 159
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lys-modified

<400> SEQUENCE: 159
tgtcttgtct ttgctgatgt ttc                                          23

<210> SEQ ID NO 160
<211> LENGTH: 23
<212> TYPE: DNA
<213> ORGANISM: artificial
<220> FEATURE:
<223> OTHER INFORMATION: synthetic

<400> SEQUENCE: 160
tgtcttgtct ttgctgatgt ttc                                          23

<210> SEQ ID NO 161
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lys-modified

<400> SEQUENCE: 161
tgtcttgtct ttgctgatgt ttc                                          23

<210> SEQ ID NO 162
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: Amino modified

<400> SEQUENCE: 162
ctcttgacct gctgtgtcga g                                            21

<210> SEQ ID NO 163
<211> LENGTH: 21
<212> TYPE: DNA
<213> ORGANISM: artificial
<220> FEATURE:
<223> OTHER INFORMATION: synthetic

<400> SEQUENCE: 163
tcccaacacc acctgctcca a                                            21

<210> SEQ ID NO 164
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lys-modified

<400> SEQUENCE: 164
caacaccacc tgctccaacc accac                                        25

<210> SEQ ID NO 165
<211> LENGTH: 23
<212> TYPE: DNA
<213> ORGANISM: artificial

<220> FEATURE:
<223> OTHER INFORMATION: synthetic

<400> SEQUENCE: 165
cttttcccaa caccacctgc tcc                                              23

<210> SEQ ID NO 166
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lys-modified

<400> SEQUENCE: 166
tgcgcttttc ccaacaccac ctgct                                            25

<210> SEQ ID NO 167
<211> LENGTH: 23
<212> TYPE: DNA
<213> ORGANISM: artificial
<220> FEATURE:
<223> OTHER INFORMATION: synthetic

<400> SEQUENCE: 167
ggcactgtac tcttcttgtc cag                                              23

<210> SEQ ID NO 168
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lys-modified

<400> SEQUENCE: 168
tctggtcttg gctgaggttt c                                                21

<210> SEQ ID NO 169
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: Amino and carboxamido modified

<400> SEQUENCE: 169
ggcaaatcac acttgtttcc cac                                              23

<210> SEQ ID NO 170
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lys-modified

<400> SEQUENCE: 170
ggcaaatcac acttgtttcc cac                                    23

<210> SEQ ID NO 171
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: Amino and carboxamide modified

<400> SEQUENCE: 171
ttcttgtcca gctgtatcca gtatg                                  25

<210> SEQ ID NO 172
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lys-modified

<400> SEQUENCE: 172
agatcctctc tctgaaatca c                                      21

<210> SEQ ID NO 173
<211> LENGTH: 24
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(24)
<223> OTHER INFORMATION: D-Lys-modified

<400> SEQUENCE: 173
tctttctcct gctcagtgat ttca                                   24

<210> SEQ ID NO 174
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lys-modified

<400> SEQUENCE: 174
aatgatgcac atcatggtgg ctg                                    23

<210> SEQ ID NO 175
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lys-modified -continued

<400> SEQUENCE: 175
ggcactgtac tcttcttgtc cag    23

<210> SEQ ID NO 176
<211> LENGTH: 26
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(26)
<223> OTHER INFORMATION: Amino modified

<400> SEQUENCE: 176
ttcatcaacc gcactctgtt tatctc    26

<210> SEQ ID NO 177
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: Amino modified

<400> SEQUENCE: 177
tggcgacgac aatggaccca attat    25

<210> SEQ ID NO 178
<211> LENGTH: 30
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(30)
<223> OTHER INFORMATION: Amino modified

<400> SEQUENCE: 178
agatgtagtt agcaatcggt ccttgttgta    30

<210> SEQ ID NO 179
<211> LENGTH: 30
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(30)
<223> OTHER INFORMATION: Amino modified

<400> SEQUENCE: 179
gggtaattga ggtaacgtag gtatcaagat    30

<210> SEQ ID NO 180
<211> LENGTH: 27
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(27)

<223> OTHER INFORMATION: Amino modified

<400> SEQUENCE: 180
tactatcgac tgacatgagg cttgtgt                                              27

<210> SEQ ID NO 181
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lys modified

<400> SEQUENCE: 181
agtccgacga tctggaattc                                                     20

<210> SEQ ID NO 182
<211> LENGTH: 19
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(19)
<223> OTHER INFORMATION: D-Lys modified

<400> SEQUENCE: 182
actggagttc agacgtgtg                                                      19

<210> SEQ ID NO 183
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lys modified

<400> SEQUENCE: 183
ctcttccgat cagatcggaa                                                     20

<210> SEQ ID NO 184
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lys modified

<400> SEQUENCE: 184
ctcttccgat cagatcggaa g                                                   21

<210> SEQ ID NO 185
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base

```
<222> LOCATION: (1)..(15)
<223> OTHER INFORMATION: D-Lys modified

<400> SEQUENCE: 185
agcgctcccc gcacc                                                    15

<210> SEQ ID NO 186
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(15)
<223> OTHER INFORMATION: D-Lys modified

<400> SEQUENCE: 186
agcgctcccc gcacc                                                    15

<210> SEQ ID NO 187
<211> LENGTH: 14
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(14)
<223> OTHER INFORMATION: D-Lys modified

<400> SEQUENCE: 187
ggggagcgct ctgt                                                     14

<210> SEQ ID NO 188
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(15)
<223> OTHER INFORMATION: D-Lys modified

<400> SEQUENCE: 188
agcgctcccc gcacc                                                    15

<210> SEQ ID NO 189
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lys modified

<400> SEQUENCE: 189
tgcatacaca ctgcccgcct                                               20

<210> SEQ ID NO 190
<211> LENGTH: 360
<212> TYPE: DNA
<213> ORGANISM: Homo sapiens

<400> SEQUENCE: 190
```

```
tagaaattag atctcttacc taaactcttc ataatgcttg ctctgatagg aaaatgagat        60
ctactgtttt cctttactta ctacacctca gatatatttc ttcatgaaga cctcacagta       120
aaaataggtg attttggtct agctacagtg aaatctcgat ggagtgggtc ccatcagttt       180
gaacagttgt ctggatccat tttgtggatg gtaagaattg aggctatttt tccactgatt       240 aaattttttgg ccctgagatg ctgctgagtt actagaaagt cattgaaggt ctcaactata       300
gtattttcat agttcccagt attcacaaaa atcagtgttc ttatttttta tgtaaataga       360

<210> SEQ ID NO 191
<211> LENGTH: 480
<212> TYPE: DNA
<213> ORGANISM: Homo sapiens

<400> SEQUENCE: 191
tagagaaggc gtacatttgt ccttccaaat gagctggcaa gtgccgtgtc ctggcaccca        60
agcccatgcc gtggctgctg gtcccccctgc tgggccatgt ctggcactgc tttccagcat      120
ggtgagggct gaggtgaccc ttgtctctgt gttcttgtcc cccccagctt gtggagcctc       180
ttacacccag tggagaagct cccaaccaag ctctcttgag gatcttgaag gaaactgaat       240
tcaaaaagat caaagtgctg ggctccggtg cgttcggcac ggtgtataag gtaaggtccc       300
tggcacaggc ctctgggctg ggccgcaggg cctctcatgg tctggtgggg agcccagagt       360
ccttgcaagc tgtatatttc catcatctac tttactcttt gtttcactga gtgtttggga       420
aactccagtg tttttcccaa gttattgaga ggaaatcttt tataaccaca gtaatcagtg       480

<210> SEQ ID NO 192
<211> LENGTH: 420
<212> TYPE: DNA
<213> ORGANISM: Homo sapiens

<400> SEQUENCE: 192
agcccaacag ctgcagggct gcggggggcgt cacagccccc agcaatatca gccttaggtg        60
cggctccaca gccccagtgt ccctcacctt cggggtgcat cgctggtaac atccacccag       120
atcactgggc agcatgtggc accatctcac aattgccagt taacgtcttc cttctctctc       180
tgtcataggg actctggatc ccagaaggtg agaaagttaa aattcccgtc gctatcaagg       240
aattaagaga agcaacatct ccgaaagcca acaggaaat cctcgatgtg agtttctgct       300
ttgctgtgtg ggggtccatg gctctgaacc tcaggcccac cttttctcat gtctggcagc       360
tgctctgctc tagaccctgc tcatctccac atcctaaatg ttcactttct atgtctttcc       420

<210> SEQ ID NO 193
<211> LENGTH: 480
<212> TYPE: DNA
<213> ORGANISM: Homo sapiens

<400> SEQUENCE: 193
aaaattcccg tcgctatcaa ggaattaaga gaagcaacat ctccgaaagc caacaaggaa        60
atcctcgatg aagcctacgt gatggccagc gtggacaacc ccacgtgtgt ccgcctgctg       120
ggcatctgcc tcacctccac cgtgcagctc atcacgcagc tcatgccctt cggctgcctc       180
ctggactatg tccgggaaca caaagacaat attggctccc agtacctgct caactggtgt       240
gtgcagatcg caaagggcat gaactacttg gaggaccgtc gcttggtgca ccgcgacctg       300
gcagccagga cgtactggt gaaaacaccg cagcatgtca agatcacaga ttttgggctg       360
gccaaactgc tgggtgcgga agagaaagaa taccatgcag aaggaggcaa agtgcctatc       420
```

```
aagtggatgg cattggaatc aattttacac agaatctata cccaccagag tgatgtctgg    480
```

<210> SEQ ID NO 194
<211> LENGTH: 420
<212> TYPE: DNA
<213> ORGANISM: Homo sapiens

<400> SEQUENCE: 194

```
ggcatctgcc tcacctccac cgtgcagctc atcacgcagc tcatgccctt cggctgcctc     60
ctggactatg tccgggaaca caaagacaat attggctccc agtacctgct caactggtgt    120
gtgcagatcg caaagggcat gaactacttg gaggaccgtc gcttggtgca ccgcgacctg    180
gcagccagga acgtactggt gaaaacaccg cagcatgtca gatcacaga ttttgggctg     240 gccaaactgc tgggtgcgga agagaaagaa taccatgcag aaggaggcaa agtgcctatc    300
aagtggatgg cattggaatc aattttacac agaatctata cccaccagag tgatgtctgg    360
agctacgggg tgaccgtttg ggagttgatg acctttggat ccaagccata tgacggaatc    420
```

<210> SEQ ID NO 195
<211> LENGTH: 239
<212> TYPE: DNA
<213> ORGANISM: Homo sapiens

<400> SEQUENCE: 195

```
ctgcaggatt cctaccggaa gcaggtggtc attgatgggg agacgtgcct gttggacatc     60
ctggataccg ccggccagga ggagtacagc gccatgcggg accagtacat gcgcaccggg    120
gagggcttcc tgtgtgtgtt tgccatcaac aacaccaagt cttttgagga catccaccag    180
tacaggtgaa ccccgtgagg ctggcccggg agcccacgcc gcacaggtgg ggccaggcc     239
```

<210> SEQ ID NO 196
<211> LENGTH: 770
<212> TYPE: DNA
<213> ORGANISM: Homo sapiens

<400> SEQUENCE: 196

```
ctgacatcta cctctagttg tacttctgtc ctctatttca ggtgttatgg gtcaagcctg      60
tttgactggc attattcatg attcctgtac cactcttgct ctctctcact ttgatctcca    120
tattccaggc ttacacaggg gtttcctcag aacgttgatg gcagttgcag gtccatataa    180
agggaccaaa gcacattgta tcctcatcta tagtcatgct gaaagtagga gaaagtgcat    240 cttattatg gcagagagaa ttttctgaac tatttatgga caacagtcaa acaacaattc     300 tttgtactt tttttttcct tagtctttct ttgaagcagc aagtatgatg agcaagcttt     360
ctcacaagca tttggtttta aattatggag tatgtgtctg tggagacgag agtaagtaaa    420
actacaggct ttctaatgcc tttctcagag catctgtttt tgtttatata gaaaattcag    480
tttcaggatc acagctaggt gtcagtgtaa actataattt aacaggagtt aagtattttt    540
gaaactgaaa acactgtagg actattcagt tatatcttgt gaaaaggaa agcaatgaag     600 ttaaaagtag aaggttacaa tgcccaaaca atagagtatt atagtaaaca aatgtctata    660
aaacattttg tgttcatgat agcaaaagag attatggcag gttcaacata acattggaat    720
aactggcctt ttcagtacaa acttatctgg aattatgaag acaaagcata              770
```

<210> SEQ ID NO 197
<211> LENGTH: 240
<212> TYPE: DNA

<213> ORGANISM: Homo sapiens

<400> SEQUENCE: 197

| ggtactggtg gagtatttga tagtgtatta accttatgtg tgacatgttc taatatagtc | 60 |
| acattttcat tattttttatt ataaggcctg ctgaaaatga ctgaatataa acttgtggta | 120 |
| gttggagctg gtggcgtagg caagagtgcc ttgacgatac agctaattca gaatcatttt | 180 |
| gtggacgaat atgatccaac aatagaggta aatcttgttt taatatgcat attactggtg | 240 |

<210> SEQ ID NO 198
<211> LENGTH: 240
<212> TYPE: DNA
<213> ORGANISM: Homo sapiens

<400> SEQUENCE: 198

| cttctcagga ttcctacagg aagcaagtag taattgatgg agaaacctgt ctcttggata | 60 |
| ttctcgacac agcaggtcaa gaggagtaca gtgcaatgag ggaccagtac atgaggactg | 120 |
| gggagggctt tctttgtgta tttgccataa ataactacta atcatttgaa gatattcacc | 180 |
| attataggtg ggtttaaatt gaatataata agctgacatt aaggagtaat tatagttttt | 240 |

<210> SEQ ID NO 199
<211> LENGTH: 300
<212> TYPE: DNA
<213> ORGANISM: Homo sapiens

<400> SEQUENCE: 199

| gtgctataac ttttttttct ttcccagaga acaaattaaa agagttaagg actctgaaga | 60 |
| tgtacctatg gtcctagtag gaaataaatg tgatttgcct tctagaacag tagacacaaa | 120 |
| acaggctcag gacttagcaa gaagttatgg aattcctttt attgaaacat cagcaaagac | 180 |
| aagacaggta agtaacactg aaataaatac agatctgttt tctgcaaaat cataactgtt | 240 |
| atgtcattta atatatcagt tttttctctca attatgctat actaggaaat aaaacaatat | 300 |

<210> SEQ ID NO 200
<211> LENGTH: 180
<212> TYPE: DNA
<213> ORGANISM: Homo sapiens

<400> SEQUENCE: 200

| aatgcaacag actttaaaga agttgtgttt tacaatgcag agagtggagg atgcttttta | 60 |
| tacattggtg agggagatcc gacaatacag attgaaaaaa atcagcaaag aagaaaagac | 120 |
| tcctggctgt gtgaaaatta aaaaatgcat tataatgtaa tctggtaagt ttaagttcag | 180 |

<210> SEQ ID NO 201
<211> LENGTH: 480
<212> TYPE: DNA
<213> ORGANISM: Homo sapiens

<400> SEQUENCE: 201

| gtgttttgc gttctctagt cactttaaga accaaatgga aggtcacact agggttttca | 60 |
| tttccattga ttatagaaag ctttaaagta ctgtagatgt ggctcgccaa ttaaccctga | 120 |
| ttactggttt ccaacaggtt cttgctggtg tgaaatgact gagtacaaac tggtggtggt | 180 |
| tggagcaggt ggtgttggga aaagcgcact gacaatccag ctaatccaga accactttgt | 240 |
| agatgaatat gatcccacca tagaggtgag gcccagtggt agcccgctga cctgatcctg | 300 |
| tctctcactt gtcggatcat ctttacccat attctgtatt aaaggaataa gaggagagaa | 360 | agtaaaaagt tattttgggt atacattcag ttatgcaata agcttaacgt gtttatagag    420 aacagttcat ttttattagc tgctgaagtt tctaaaacct gtccagtttt taacagttct    480

<210> SEQ ID NO 202
<211> LENGTH: 480
<212> TYPE: DNA
<213> ORGANISM: Homo sapiens

<400> SEQUENCE: 202
tgggcttgaa tagttagatg cttatttaac cttggcaata gcattgcatt ccctgtggtt     60
tttaataaaa attgaacttc cctccctccc tgccccctta ccctccacac ccccaggatt    120
cttacagaaa acaagtggtt atagatggtg aaacctgttt gttggacata ctggatacag    180
ctggacaaga agagtacagt gccatgagag accaatacat gaggacaggc gaaggcttcc    240
tctgtgtatt tgccatcaat aatagcaagt catttgcgga tattaacctc tacaggtact    300
aggagcatta ttttctctga aaggatgatc tttgtgttct gaatctttat ggggaaatga    360
ggttaccaca ctagggaaga tagagctttt taattatggg aagagttggt tttaggttgt    420
ttgacattga gaatctaggg taattactga aagttaatac tggaatttat tttacataat    480

<210> SEQ ID NO 203
<211> LENGTH: 420
<212> TYPE: DNA
<213> ORGANISM: Homo sapiens

<400> SEQUENCE: 203
tggatacagc tggacaagaa gagtacagtg ccatgagaga ccaatacatg aggacaggcg     60
aaggcttcct ctgtgtattt gccatcaata atagcaagtc atttgcggat attaacctct    120
acagggagca gattaagcga gtaaaagact cggatgatgt acctatggtg ctagtgggaa    180
acaagtgtga tttgccaaca aggacagttg atacaaaaca agcccacgaa ctggccaaga    240
gttacgggat tccattcatt gaaacctcag ccaagaccag acagggtgtt gaagatgctt    300
tttacacact ggtaagagaa atacgccagt accgaatgaa aaaactcaac agcagtgatg    360
atgggactca gggttgtatg ggattgccat gtgtggtgat gtaacaagat acttttaaag    420

<210> SEQ ID NO 204
<211> LENGTH: 360
<212> TYPE: DNA
<213> ORGANISM: Homo sapiens

<400> SEQUENCE: 204
tgtaaaattt attgaaaatg tatttgcttt ttctgtaaat catctgtgaa tccagagggg     60
aaaaatatga caaagaaagc tatataagat attattttat tttacagagt aacagactag    120
ctagagacaa tgaattaagg gaaaatgaca agaacagct caaagcaatt tctacacgag     180
atcctctctc tgaaatcact gagcaggaga agattttct atggagtcac aggtaagtgc    240
taaaatggag attctctgtt tctttttctt tattacagaa aaaataactg aatttggctg    300
atctcagcat gttttttacca tacctattgg aataaataaa gcagaattta catgattttt    360

<210> SEQ ID NO 205
<211> LENGTH: 300
<212> TYPE: DNA
<213> ORGANISM: Homo sapiens

<400> SEQUENCE: 205

```
tagctattcg acagcatgcc aatctcttca taaatctttt ctcaatgatg cttggctctg      60
gaatgccaga actacaatct tttgatgaca ttgcatacat tcgaaagacc ctagccttag     120
ataaaactga gcaagaggct ttggagtatt tcatgaaaca aatgaatgat gcacatcatg     180
gtggctggac aacaaaaatg gattggatct tccacacaat taaacagcat gcattgaact     240
gaaaagataa ctgagaaaat gaaagctcac tctggattcc acactgcact gttaataact     300

<210> SEQ ID NO 206
<211> LENGTH: 490
<212> TYPE: DNA
<213> ORGANISM: Homo sapiens

<400> SEQUENCE: 206
gttgtaaatc tttgtaacac ttcaaaaagc tatattgtat ttatatttta aaataaattt      60
cagggtaaaa taataataaa gcaaaggtac ctagtaaagt ttttaactat tttaaaggct     120
tgaagagtgt cgaattatgt cctctgcaaa aaggccactg tggttgaatt gggagaaccc     180
agacatcatg tcagagttac tgtttcagaa caatgagatc atctttaaaa atggggatgg     240
taaggaagag tattaatgag cttatgatgc atgaatttag ctatcttttt atacacagga     300
tatttatgaa ccatgaaaac tactgaaagc catttaagga atatacacat gtgataaaat     360
atgtaatatt tatcagatgt cttgaccttt gaaatatgca tgtataatca atgaaaagaa     420
aagaagtact aggtttagat cagaagtcct gaaatcagtt ttttgttttt tctttttcct     480
gttccctgcc                                                            490
```

DNA MUTATION DETECTION EMPLOYING ENRICHMENT OF MUTANT POLYNUCLEOTIDE SEQUENCES AND MINIMALLY INVASIVE SAMPLING

This application claims the priority benefit under 35 U.S.C. section 119 of U.S. Provisional Patent Application No. 62/010,339 entitled "Method For Enrichment Of Target Mutant Polynucleotide Sequences" filed on Jun. 10, 2014; U.S. Provisional Patent Application No. 62/010,357 entitled "Detection Of Multiple Mutations In A Single Tube Using Qclamp Assay Qclamp Mplex" filed on Jun. 10, 2014; and U.S. Provisional Patent Application No. 62/010,359 entitled "Liquid Biopsy" filed on Jun. 10, 2014; which are in their entirety herein incorporated by reference.

FIELD OF THE INVENTION

The present invention relates to DNA mutation detection. The invention further relates to enrichment of mutant polynucleotide sequences. The present invention further relates to minimally invasive sampling and analysis of mutations in clinical samples.

The instant invention also relates to a method for determining whether a target polynucleotide sequence contained in a nucleic acid sample has nucleotide variation(s) in a selected region thereof, the steps of which involve the use of a pair of primers that allows the formation of a PCR product having a sequence covering that of the selected region of the target polynucleotide sequence via a PCR process, and a peptide nucleic acid (PNA) that acts as a PCR clamp as well as a sensor probe. This invention also relates to a kit for use in determining the presence of nucleotide variation(s) in the target polynucleotide sequence, which comprises the pair of primers and the PNA.

The present embodiments relate to precision molecular diagnostics, and in particular, to compositions in detecting sequence variants, such as SNPs, insertions deletions, and altered methylation patterns, from samples. The embodiments disclosed herein can be used to detect (and quantify) sequence variants present in samples that include an excess of wild-type sequences.

BACKGROUND OF THE INVENTION

Polymerase chain reaction (PCR) is a widely used technique for the detection of pathogens. The technique uses a DNA polymerase used to amplify a piece of DNA by in vitro enzymatic replication. The PCR process generates DNA that is used as a template for replication. This results in a chain reaction that exponentially amplifies the DNA template.

Technologies for genomic detection most commonly use DNA probes to hybridize to target sequences. To achieve required sensitivity, the use of PCR to amplify target sequences has remained standard practice in many labs. While PCR has been the principle method to identify genes associated with disease states, the method has remained confined to use within a laboratory environment. Most current diagnostic applications that can be used outside of the laboratory are based on antibody recognition of protein targets and use ELISA-based technologies to signal the presence of a disease. These methods are fast and fairly robust, but they can lack the specificity associated with nucleic acid detection.

With the advent of molecular diagnostics and the discovery of numerous nucleic acid biomarkers useful in the diagnosis and treatment of conditions and diseases, detection of nucleic acid sequences, and sequence variants, mutations and polymorphisms has become increasingly important. In many instances, it is desirable to detect sequence variants or mutations (which may in some instances, differ by one a single nucleotide) present in low copy numbers against a high background of wild-type sequences. For example, as more and more somatic mutations are shown to be biomarkers for cancer prognosis and prediction of therapeutic efficacy, the need for efficient and effective methods to detect rare mutations in a sample is becoming more and more critical. In the case in which one or more allelic variants is/are present in low copy number compared to wild-type sequences, the presence of excess wild-type target sequence creates challenges to the detection of the less abundant variant target sequence. Nucleic acid amplification/detection reactions almost always are performed using limiting amounts of reagents. A large excess of wild-type target sequences, thus competes for and consumes limiting reagents. As a result amplification and/or detection of rare mutant or variant alleles under these conditions is substantially suppressed, and the methods may not be sensitive enough to detect the rare variants or mutants. Various methods to overcome this problem have been attempted. These methods are not ideal, however, because they either require the use of a unique primer for each allele, or the performance of an intricate melt-curve analysis. Both of these shortcomings limit the ability and feasibility of multiplex detection of multiple variant alleles from a single sample.

BRIEF DESCRIPTION OF THE FIGURES

FIG. 4 is a representative fluorophore spectral data and quencher selection guide.

SUMMARY OF THE INVENTION

Figure 1:
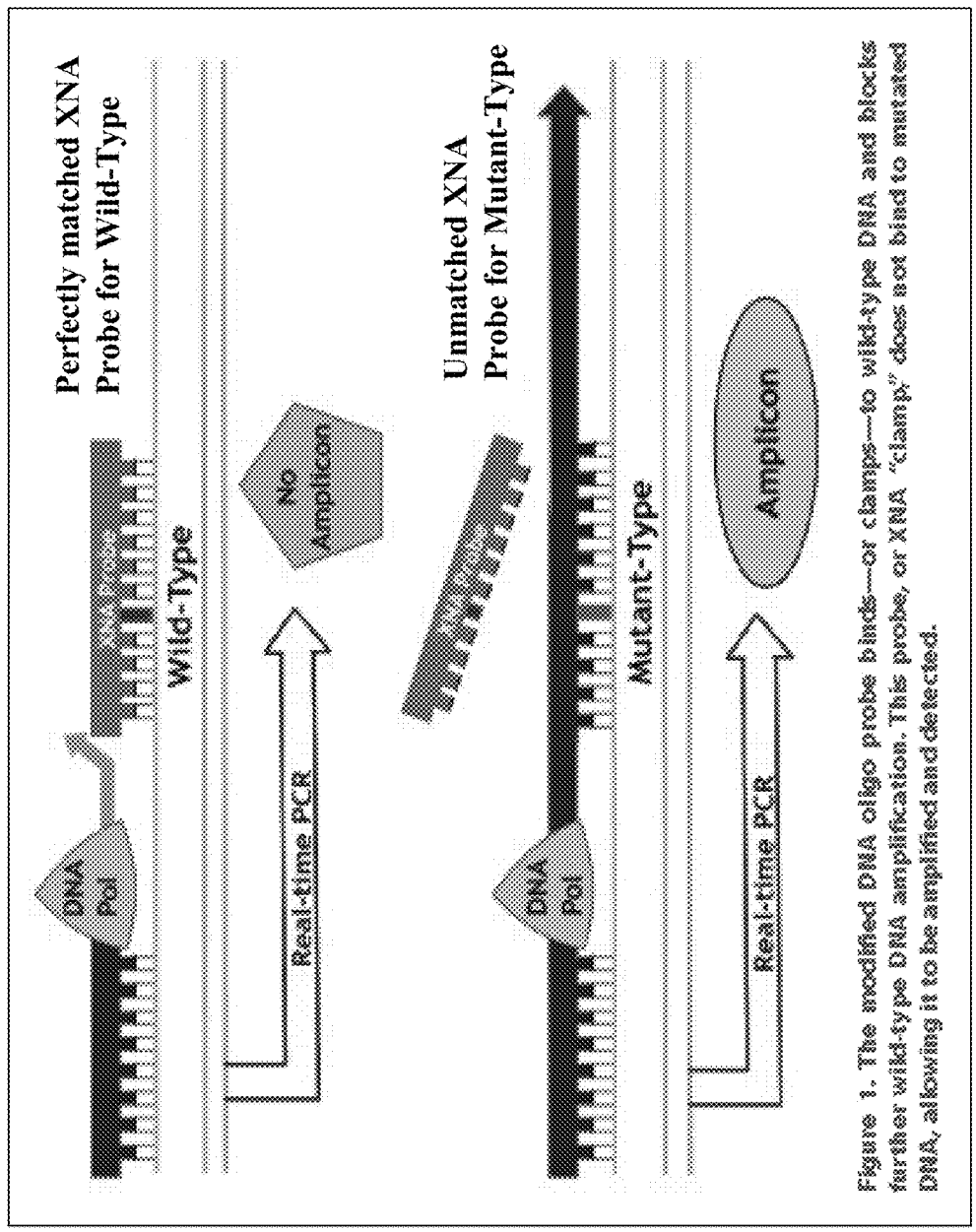
FIG. 1 illustrates the mechanism of the XNA clamping process.
Figure 2:
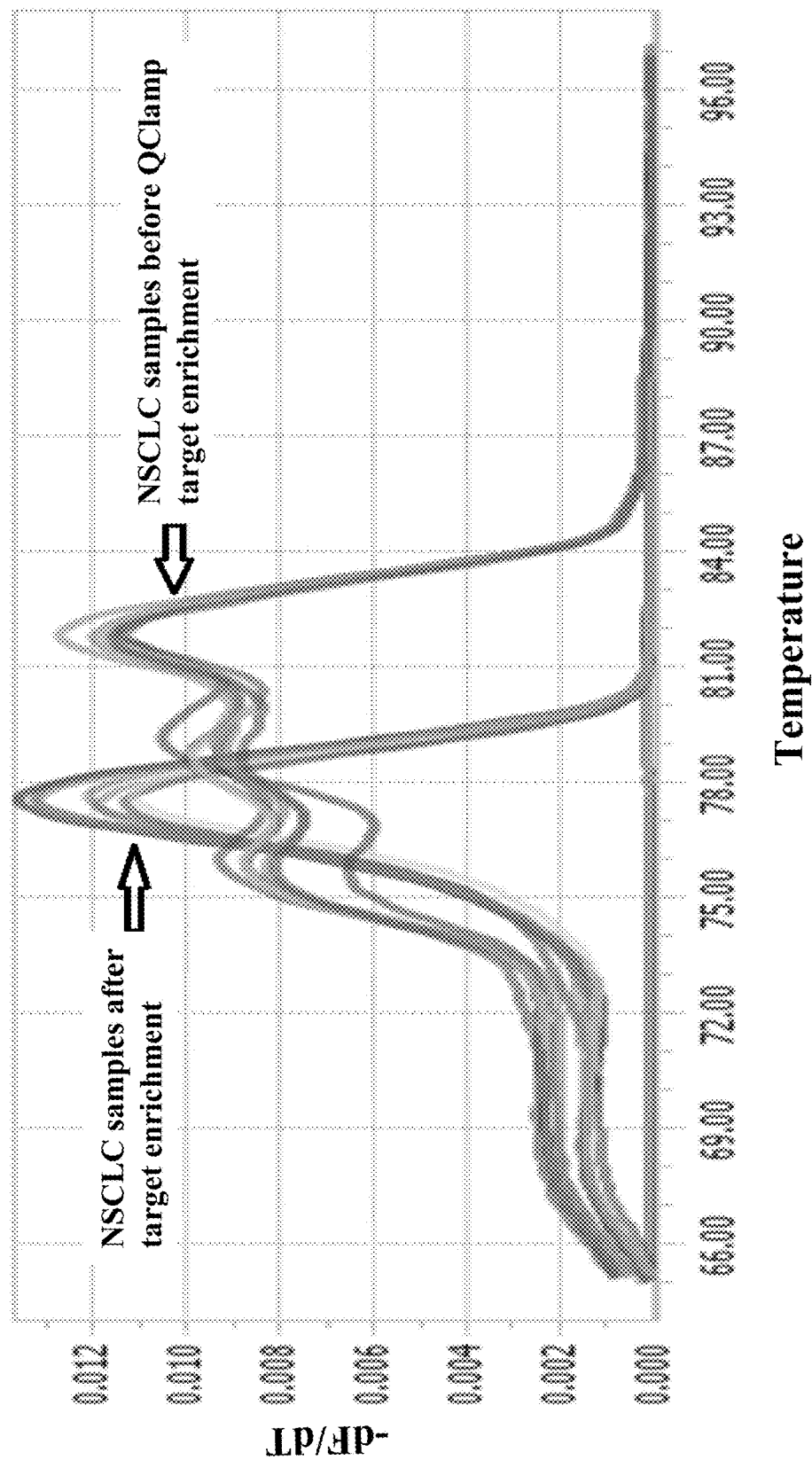
FIG. 2 shows the differential melting temperature (Tm) between the XNA clamp bound to mutant templates vs wild type templates.

Detection of rare sequence variants in biological samples presents numerous challenges. The methods and kits disclosed herein provide for improved, efficient means to detect rare mutations within a high background of wild-type allelic sequences using real-time amplification methods.

The instant invention provides a method for enriching a target polynucleotide sequence containing a genetic variation said method comprising: (a) providing two primers targeted to said target polynucleotide sequence; (b) providing a target specific xenonucleic acid clamp oligomer specific for a wildtype polynucleotide sequence; (c) generating multiple amplicons using PCR under specific temperature cycling conditions; and (d) detecting said amplicons.

The invention also relates to a method for enriching multiple target polynucleotide sequences containing a genetic variation said method comprising: (a) providing a library of amplifying primers targeted to said multiple target polynucleotide sequence; (b) providing a library of target specific xenonucleic acid clamp oligomer specific for multiple wildtype polynucleotide sequences; (c) generating multiple amplicons using PCR under specific temperature cycling conditions; and (d) detecting said amplicons.

The invention further relates to a method for conducting a minimally invasive biopsy in a mammalian subject suspected of a having a neoplastic disease, said method comprising: (a) sampling of target polynucleotides derived from said mammalian subject; (b) providing a library of amplifying primers targeted to said multiple target poly-nucleotide sequence; (c) providing a library of target specific xenonucleic acid clamp oligomer specific for multiple wild-type polynucleotide sequences; (d) generating multiple amplicons using PCR under specific temperature cycling conditions; and (e) detecting said amplicons.

The invention is also directed to means and methodology for the rapid isolation of genetic material from biological fluids and the sensitive detection of somatic and germ-line mutations present in circulating cells and cell-free genetic material obtained from said biological fluids using gene amplification and xeno-nucleic acid (XNA) clamping.

This invention provides a method for determining whether a target polynucleotide sequence contained in a nucleic acid sample has nucleotide variation(s) in a selected region thereof, comprising the steps of: providing a pair of a first primer and a second primer which allows the formation of a PCR product having a sequence covering that of the selected region of the target polynucleotide sequence via a PCR process, the first primer having a sequence identical to that of a first region located upstream of the selected region of the target polynucleotide sequence, the second primer having a sequence based on that of a second region located downstream of the selected region of the target polynucleotide sequence, wherein the 6'-end of the sequence of the first region is spaced apart from the 5'-end of the sequence of the sequence of the selected region by 30 nucleotides or more;

providing a detectable peptide nucleic acid probe having a sequence that complements fully the sequence of the selected region of the target polynucleotide sequence having no nucleotide variation(s) therein, such that hybridization of the detectable peptide nucleic acid probe to the selected region of the target polynucleotide sequence having no nucleotide variation(s) results in the formation of a duplex having a melting temperature;

determining the melting temperature of the duplex;
admixing the detectable peptide nucleic acid probe and the pair of the first primer and the second primer with the nucleic acid sample to form a mixture;
subjecting the mixture to a PCR process including an extension reaction set to run at a temperature lower than the melting temperature of the duplex by 5 to 20° C., such that a mixture of PCR products is obtained; and
subjecting the mixture of PCR products thus-obtained to a melting analysis to determine melting temperatures of the PCR products, wherein the presence of at least one melting temperature lower than the melting temperature of the duplex is indicative of the nucleotide variation(s) in the selected region of the target polynucleotide sequence contained in the nucleic acid sample.

The invention also provides a kit for determining whether a target polynucleotide sequence contained in a nucleic acid sample has nucleotide variation(s) in a selected region thereof, comprising: a detectable peptide nucleic acid probe having a sequence that complements fully the sequence of the selected region of the target polynucleotide sequence having no nucleotide variation(s) therein, such that hybridization of the detectable peptide nucleic acid probe to the selected region of the target polynucleotide sequence having no nucleotide variation(s) results in the formation of a duplex having a melting temperature;

a pair of a first primer and a second primer which allows the formation of a PCR product having a sequence covering that of the selected region of the target polynucleotide sequence via a PCR process, the first primer having a sequence identical to that of a first region located upstream of the selected region of the target polynucleotide sequence, the second primer having a sequence based on that of a second region located downstream of the selected region of the target polynucleotide sequence, wherein the 5'-end of the sequence of the first region is spaced apart from the 5'-end of the sequence of the sequence of the selected region by 30 nucleotides or more; and an instruction sheet providing guidance for a user to use the detectable peptide nucleic acid probe and the pair of the first primer and the second primer in a method as described above.

DETAILED DESCRIPTION OF THE INVENTION

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y". Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

In a first embodiment, the present invention relates to compositions and methods for the selective enrichment of low-abundance polynucleotides in a sample. These methods use xeno-nucleic acid (XNA) nucleobase oligomers to selectively block DNA polymerase activity on high abundance wild-type DNA templates, thereby resulting in enrichment of less abundant mutated DNA templates present in a biological sample during a polymerase chain reaction (PCR). The methodology of the present invention can be used to improve DNA sequencing (Sanger sequencing and Pyrosequencing) and also enhance cDNA library preparation for next generation DNA sequencing (NGS).

Utilizing xeno-nucleic acid (XNA) clamping probes in the PCR mediated amplification of DNA templates, only target genetic material that has a variation, e.g. single nucleotide polymorphism (SNP), gene deletion or insertion and/or translocation or truncation is amplified in the oligonucleotide primer directed polymerase chain reaction (qPCR).

The XNA probe clamping sequences are designed to bind specifically by Watson-Crick base pairing to abundant wild-type sequences in the DNA templates derived from the biological sample of interest. The presence of the XNA probes in the PCR primer mix employed for the target amplification reaction causes inhibition of the polymerase mediated amplification of wild-type templates but does not impede the amplification of mutant template sequences.

The mechanism of the XNA clamping process is depicted in FIG. 1. As shown in FIG. 1, the modified DNA oligo probe binds or clamps to wild type DNA and blocks further wild type amplification. This probe or XNA "clamp" does not bind to mutated DNA, allowing it to be amplified and detected.

The suppression of wild-type (wt) template amplification and amplification of only mutant templates is achieved because there is a differential melting temperature (Tm) between the XNA clamp bound to mutant templates vs wild type templates:

Tm(XNA mutant template)<<Tm(XNA wt template)

The Tm differential is as much as 15-20° C. for the XNA clamp probes. So that during the PCR process only mutant templates are amplified.

The methods disclosed herein can be used to analyze nucleic acids of samples. The term "sample" as described herein can include bodily fluids (including, but not limited to, blood, urine, feces, serum, lymph, saliva, anal and vaginal secretions, perspiration, peritoneal fluid, pleural fluid, effusions, ascites, and purulent secretions, lavage fluids, drained fluids, brush cytology specimens, biopsy tissue (e.g., tumor samples), explanted medical devices, infected catheters, pus, biofilms and semen) of virtually any organism, with mammalian samples, particularly human samples.

Amplification primers useful in the embodiments disclosed herein are preferably between 10 and 45 nucleotides in length. For example, the primers can be at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length. Primers can be provided in any suitable form, included bound to a solid support, liquid, and lyophilized, for example. In some embodiments, the primers and/or probes include oligonucleotides that hybridize to a reference nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under stringent conditions or standard PCR conditions as discussed below. As used herein, the term "standard PCR conditions" include, for example, any of the PCR conditions disclosed herein, or known in the art, as described in, for example, PCR 1: A Practical Approach, M. J. McPherson, P. Quirke, and G. R. Taylor, Ed., (c) 2001, Oxford University Press, Oxford, England, and PCR Protocols: Current Methods and Applications, B. White, Ed., (c) 1993, Humana Press, Totowa, N.J. The amplification primers can be substantially complementary to their annealing region, comprising the specific variant target sequence(s) or the wild type target sequence(s). Accordingly, substantially complementary sequences can refer to sequences ranging in percent identity from 100, 99, 98, 97, 96, 95, 94, 93, 92, 91, 90, 89, 85, 80, 75 or less, or any number in between, compared to the reference sequence. Conditions for enhancing the stringency of amplification reactions and suitable in the embodiments disclosed herein, are well-known to those in the art. A discussion of PCR conditions, and stringency of PCR, can be found, for example in Roux, K. "Optimization and Troubleshooting in PCR," in Pcr Primer: A Laboratory Manual, Diffenbach, Ed. © 1995, Cold Spring Harbor Laboratory Press, Cold Spring Harbor, N.Y.; and Datta, et al. (2003) Nucl. Acids Res. 31(19):5590-5597.

Provided herein are methods useful in the detection of sequence variants, i.e., insertions, deletions, nonsense mutations, missense mutations, and the like. In the methods for detecting allelic variants or variant target sequences disclosed herein, the sample, which comprises the nucleic acids to be analyzed, are contacted with an amplification primer pair, i.e., comprising a forward primer and a reverse primer that flank the target sequence or target region containing a sequence of interest {e.g., a wild-type, mutant, or variant allele sequence) to be analyzed. By "flanking" the target sequence, it is understood that the variant or wild-type allelic sequence is located between the forward and reverse primers, and that the binding site of neither the forward nor reverse primer comprises the variant or wild-type allelic sequence to be assessed. For example, in some embodiments, the variant or wild-type allelic sequence to be assessed is removed from or positioned away from the 3' end of either oligonucleotide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more, e.g., 100 or more, 200 or more, 300 or more, 400 or more, 500 or more, etc., nucleotides. Amplification primers that flank, but that do not overlap with, the variant target sequence or the wild-type target sequence are thus not "allele-specific" amplification primers, and are capable of amplification of various different alleles or variants of a sequence of interest. Thus, in some embodiments, the amplification primers are configured to amplify various mutant or variant alleles and wild type alleles non-preferentially. As discussed in further detail below, the addition of XNA or PNA to an amplification reaction suppresses the amplification of wild-type target sequences and enables preferential amplification of non-wild-type, e.g., variant, mutant or rare variant alleles. FIG. 1 is a depictions of exemplary method according to the embodiments disclosed herein for the detection of sequence variants. As shown in FIG. 1, amplification primers (i.e., forward primer 1 and reverse primer 2) flank the wild type and mutant allele sequences of interest, and comprise sequences common to both wild-type and mutant or variant allele sequences. Accordingly, as shown in FIG. 1, in contrast to methods that utilize allele-specific amplification primers to achieve preferential amplification of rare sequences, the present methods advantageously enable the simultaneous amplification of multiple variant sequences, using a single amplification primer pair.

In a second embodiment, the invention relates to compositions and methods for the detection of genetic variations (mutations) in DNA templates derived from biological samples with xeno-nucleic acid clamping probes. The first method employs multi-color fluorescence detection using locus specific fluorescent hybridization probes (Hyb Probes), hydrolysis (TaqMan or ZEN) probes or molecular beacons. The second method employs mutant specific amplicon capture probes immobilized on multiple bar-coded capture beads.

Current XNA clamping qPCR methodologies utilize a single tube—single mutation detection format it is preferable to detect multiple genetic variations in a single tube thus reducing the complexity of the assay and the amount of template DNA required for analysis.

This second embodiment of the invention is directed to the use of locus specific fluorescent probes designed to detect the genetic variant (mutant) amplicons generated during the XNA clamping PCR reaction. This second embodiment discloses locus specific probes that bind to mutant specific amplicons at a region upstream or downstream from the site of the mutation to be detected. Furthermore, the second embodiment discloses the use of multiplexed XNA clamping qPCR reactions that are able to detect multiple mutations (up to a maximum of 6) in one PCR reaction tube using fluorescence detection methodology.

In a third embodiment of the invention, there is provided a method the rapid isolation of genetic material present in circulating cells and also cell-free genetic material from biological fluids and the determination of genetic variations in those cells and biological fluids. Such biological fluids include: blood, serum, plasma, saliva, mucus, urine, sputum, semen or other biological secretions. In this embodiment, the invention also provides the detection of somatic and germ-line mutations in the genetic material derived from these biological fluids utilizing gene amplification and xenonucleic acid clamping.

Figure 6:
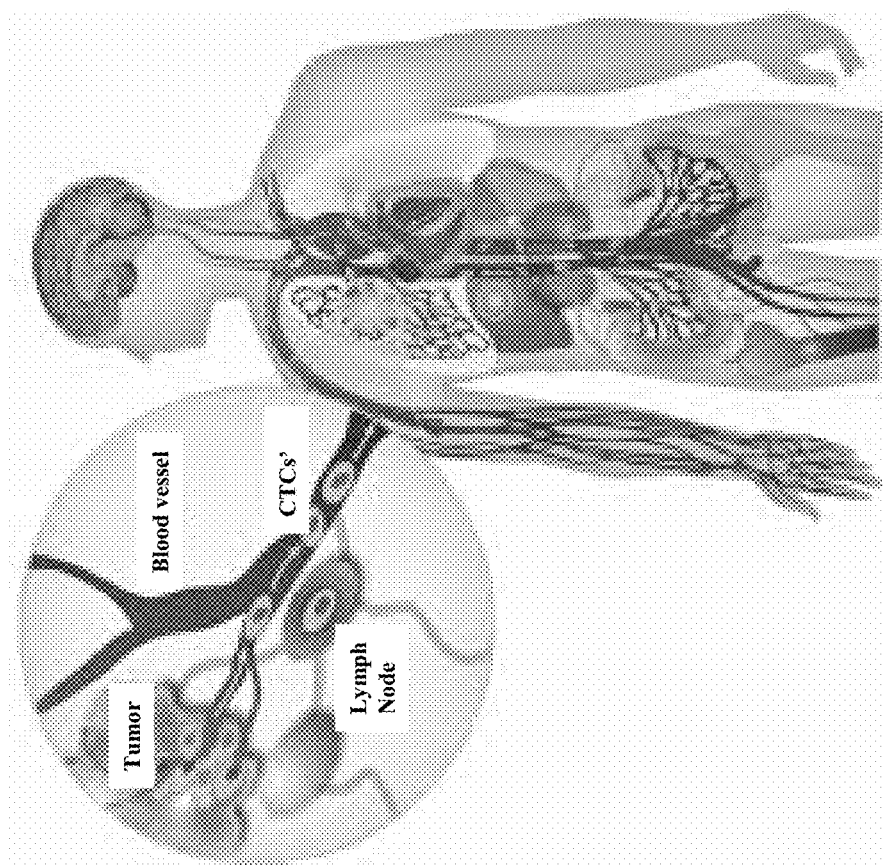
FIG. 6 is a schematic illustrating how circulating tumor cells (CTC's) and cell-free DNA (cfDNA) derived from tumor cells are present in the peripheral blood of cancer patients

Circulating tumor cells (CTC's) and cell-free DNA (cfDNA) derived from tumor cells are present in the peripheral blood of cancer patients (See FIG. 6). Tumor derived DNA can also be found in the urine and even the saliva of cancer patients.

In general circulating free DNA is smaller in size than DNA derived directly from a surgical biopsy or FFPE sample. This embodiment also describes a novel sample treatment procedure that utilizes a novel lysis reagent called QZol™. QZol™ sample lysis is a direct one tube procedure and an aliquot of the lysate is used directly in molecular genetic and cytogenetic analysis procedures such as PCR, RTPCR, FISH, Next Generation Sequencing (NGS) and branched DNA (bDNA) assays. The QZol™ procedure eliminates the tedious multistep preanalytical processing that is currently used in Molecular Pathology and Cytogenetic analysis.

The lysis reagent is a 50% solution (A) containing chaotropic salts and detergent (nonionic, anionic, cationic or zwitterionic) and a 50% solution (B) containing neutralizing reagents and stabilizers.

This invention also concerns to the specific amplification of genetic variant templates from the isolated genetic material described above. Only target genetic material that has a variation, e.g. single nucleotide polymorphism (SNP), gene deletion or insertion and/or translocation or truncation is amplified in a quantitative primer directed polymerase chain reaction (qPCR). This is achieved utilising xenonucleic acid (XNA) probe clamping sequences that have been designed to bind specifically by Watson-Crick base pairing to wild-type sequences in the sample. The presence of the XNA probes in the qPCR primer mix employed for the target amplification reaction causes inhibition of the polymerase mediated amplification of wild-type templates but does not impede the amplification of mutant template sequences.

The mechanism of the XNA clamping process is depicted in FIG. 1.

The suppression of wild-type (wt) template amplification and amplification of only mutant templates is achieved because there is a differential melting temperature (Tm) between the XNA clamp bound to mutant templates vs wt templates:

$$Tm(XNA \text{ mutant template}) << Tm(XNA \text{ wt template})$$

The Tm differential is as much as 15-20° C. for the XNA clamp probes. So that during the qPCR process only mutant templates are amplified.

The methods disclosed herein can be used in the detection of numerous allelic variants, including nonsense mutations, missense mutations, insertions, deletions, and the like. Owing to the advantageous sensitivity and specificity of detection afforded by the methods disclosed herein, the methods can detect the presence of a rare allelic variant within a sample, amongst a high wild-type background. Accordingly, although the skilled artisan will appreciate that the methods disclosed herein can be used in a variety of settings to detect, e.g., germline mutations, the methods are particularly well-suited for use in the detection of somatic mutations, such as mutations present in tumors. Non-limiting examples of rare, somatic mutations useful in the diagnosis, prognosis, and treatment of various tumors include, for example, mutations in ABL, AKT1, AKT2, ALK, APC, ATM, BRAF, CBL, CDH1, CDK 2A, CEBPA, CRLF2, CSF1R, CTNNB1, EGFR, ERBB2, EZH2, FBXW7, FGFR, FGFR2, FGFR3, FLT3, FOXL2, GATA1, GATA2, GNAQ, GNAS, HNF1A, HRAS, IDH1, IDH3, JAK2, KIT, KRAS, MEK1, MET, MPL, NF2, NOTCH 1, NOTCH2, NPM, NRAS, PC A3, PDGFRA, PIK3CA, PIK3R1, PIK3R5, PTCH1, PTEN, PTPN1 1, RBI, RET, RUNX1, SMAD4, SMARCB, SMO, STK11, TET2, P53, TSHR, VHL, WT1, and others. Exemplary mutant alleles associated with cancer useful in the embodiments disclosed herein include, but are not limited to those described in publications listed on the world wide web site for COSMIC (Catalogue Of Somatic Mutations In Cancer).

EXAMPLES

Example 1

The kit described in great detail in this Example is a KRAS mutation detection kit. However, the same type of kit may be assembled to detect mutations in NRAS, EGFR, BRAF, PIK3CA, JAK2, as well as other genes of importance in precision molecular diagnostics.

QCLAMP™ Technology for Mutation Detection

The QCLAMP™ KRAS Mutation Detection Kit is based on xenonucleic acid (XNA) mediated PCR clamping technology. XNA is a synthetic DNA analog in which the phosphodiester backbone has been replaced by a repeat formed by units of (2-aminoethyl)-glycine. XNAs hybridize tightly to complementary DNA target sequences only if the sequence is a complete match. Binding of XNA to its target sequence blocks strand elongation by DNA polymerase. When there is a mutation in the target site, and therefore a mismatch, the XNA:DNA duplex is unstable, allowing strand elongation by DNA polymerase. Addition of an XNA, whose sequence with a complete match to wild-type DNA, to a PCR reaction, blocks amplification of wild-type DNA allowing selective amplification of mutant DNA. XNA oligomers are not recognized by DNA polymerases and cannot be utilized as primers in subsequent real-time PCR reactions.

DNA Isolation

Human genomic DNA must be extracted from tissue or blood, or fixed paraffin-embedded tissue prior to use. Several methods exist for DNA isolation. For consistency, we recommend using a commercial kit, such as Qiagen DNA extraction kit (QIAamp DNA FFPE Tissue Kit, cat No. 56404, for paraffin embedded specimens; DNeasy Blood & Tissue kit, cat. No. 69504 or 69506, for tissue and blood specimens). Follow the genomic DNA isolation procedure according to manufacturer's protocol. Sufficient amounts of DNA can be isolated from FFPE blocks or fresh frozen sections (approx. 2-10 μg).

This QCLAMP™ assay requires a total of 30-60 ng of DNA per sample (5-10 ng/reaction). After DNA isolation, measure the concentration using spectrophotometric analysis (i.e. Nanodrop or UV spectrophotometer) and dilute to it to 1.25-2.5 ng/μl. Make sure A260/A230 value is greater than 2.0 and A260/A280 value between 1.8 and 2.0.

Preparation of Reagents

Each kit contains enough material to run 3 sets (10-sample test kit) or 6 sets (30-sample test kit) of Clamping Controls, Positive Controls and Non-Template Controls. Thaw all Primers, XNAs, Positive Control, WT Clamping Control, water and 2×PCR Mastermix provided. Thaw all reaction mixes at room temperature for a minimum of 1 hour. Vortex all components except the PCR Master Mix the reaction mixes for 5 sec and perform a quick spin. The PCR Master Mix should be mixed gently by inverting the tube a few times. Do not leave kit components at room temperature for more than 4 hours. After thawing, keep materials on ice at all times. The PCR reactions are set up in a total volume of 20 μl/reaction.

Table 1 shows the component volumes for each 20 ul reaction.

TABLE 1

QCLAMP™ Sample DNA Preparation Protocol

| Components | Volume/Reaction |
|---|---|
| 2X PCR Master mix | 10 μl |
| Primer Mix | 4 μl |
| XNA | 2 μl |
| DNA sample or Controls | 4 μl |
| Total volume | 20 μl |

For accuracy, 2×PCR Mastermix, primers and XNA should be pre-mixed into assay mixes as described in Table 2 below.

Preparation of Assay Mixes

IMPORTANT: Assay mixes should be prepared just prior to use. Do not store assay mixes. Prepare and keep assay mixes on ice, until ready for per. Label 7 micro centrifuge tubes (not provided) according to each corresponding reaction mix shown in Table 2.

TABLE 2

Preparation of Assay Mixes

| | Volume of 2X PCR Master Mix | Volume of Primer Mix | Volume of XNA (†use water for ext control) |
|---|---|---|---|
| Ext Control Mix | 10 μl × (*n + 1) | 4 μl × (*n + 1) | 2 μl × (*n + 1) |
| G12 Mix | 10 μl × (*n + 1) | 4 μl × (*n + 1) | 2 μl × (*n + 1) |
| G13 Mix | 10 μl × (*n + 1) | 4 μl × (*n + 1) | 2 μl × (*n + 1) |
| A59 Mix | 10 μl × (*n + 1) | 4 μl × (*n + 1) | 2 μl × (*n + 1) |
| Q61 Mix | 10 μl × (*n + 1) | 4 μl × (*n + 1) | 2 μl × (*n + 1) |
| K117 Mix | 10 μl × (*n + 1) | 4 μl × (*n + 1) | 2 μl × (*n + 1) |
| A146 Mix | 10 μl × (*n + 1) | 4 μl × (*n + 1) | 2 μl × (*n + 1) |

*n = number of reactions (DNA samples plus 3 controls). Prepare enough for 1 extra sample (n + 1) to allow for sufficient overage for the PCR set.
†Use 2 ul of water provided in the kit as the Ext Control Mix does not require XNA. For accuracy, do not pipette less than 10 ul of the XNA.

Prepare sufficient working assay mixes for the DNA samples, one KRAS Mixed Positive Control, one Nuclease-Free Water for no template control, and one WT Clamping Control, according to the volumes in Table 2. Include reagents for 1 extra sample to allow sufficient overage for the PCR set up. The master mixes contain all of the components needed for PCR except the sample.

Each sample requires one reaction for each mutation site detected by the kit and an external control. The External Control uses Exon 5 primers to determine if an appropriate level of amplifiable DNA is present in the sample, and ensures that that the supplied primers and polymerase are working properly on the sample. The KRAS Codon-Specific kit requires a total of 7 reactions for each sample.

A set of clamping controls must be run with each of the 7 reaction mixes, every time the assay is run. Clamping Controls use wild-type DNA as the template. Wild-type DNA should have no mutations, therefore the XNA probes will bind strongly, blocking the polymerase from making amplicons. However, the External Control Mix with the Clamping Control should make amplicons efficiently, providing another way to monitor performance of the primers, polymerase, and sample.

A set of positive controls must also be run with each of the 7 reaction mixes, every time the assay is run. The Positive Control contains one mutant template for each reaction mix. Positive controls contain mutations; therefore XNA probes will not bind, allowing amplification of the mutant template. Positive controls must show the appropriate values for the reaction to be valid.

A set of no template control (tube NTC) is run with each of the 7 reaction mixes every time the assay is run. Nuclease-Free Water is used in the place of template. The NTC serves as a negative control and assesses potential contamination during assay set-up.

Further quantities of KRAS Wild-Type Genomic Reference DNA Control, and Positive Control mixes can be purchased as a separate item, if desired.

Suggested Run Layout (96-Well Plate, Tube Strips, or Tubes)

Gently vortex the assay mixes for 5 sec and do a quick spin. Add 16 μl of the appropriate assay mix to the plate or tubes. Add 4 μl of template. Prepare and keep on ice until ready for PCR.

In the case of 96-well plates, the exact plate layout can be set to the user's preference. However, take care to remember which wells are for which reaction mixes, to ensure that all potential detected mutations and controls are processed properly.

Table 3 is a suggested plate set-up for a single experiment analyzing 3 unknown samples.

TABLE 3

Suggested Plate Layout

| | 1 | 2 | 3 | 4 | 5 | 6 |
|---|---|---|---|---|---|---|
| A | NTC Ext Ctrl Mix | PC Ext Ctrl Mix | CC Ext Ctrl Mix | S1 Ext Ctrl Mix | S2 Ext Ctrl Mix | S3 Ext Ctrl Mix |
| B | NTC G12 Mix | PC G12 Mix | CC G12 Mix | G12 Mix | G12 Mix | G12 Mix |
| C | NTC G13 Mix | PC G13 Mix | CC G13 Mix | S1 G13 Mix | S2 G13 Mix | S3 G13 Mix |
| D | NTC A59 Mix | PC A59 Mix | CC A59 Mix | S1 A59 Mix | S2 A59 Mix | S3 A59 Mix |

TABLE 3-continued

Suggested Plate Layout

| | 1 | 2 | 3 | 4 | 5 | 6 |
|---|---|---|---|---|---|---|
| E | NTC Q61 Mix | PC Q61 Mix | CC Q61 Mix | S1 Q61 Mix | S2 Q61 Mix | S3 Q61 Mix |
| F | NTC K117 Mix | PC K117 Mix | CC K117 Mix | S1 K117 Mix | S2 K117 Mix | S3 K117 Mix |
| G | NTC A146 Mix | PC A146 Mix | CC A146 Mix | S1 A146 Mix | S2 A146 Mix | S3 A146 Mix |

PC: Positive Control,
NTC: No Template Control (water),
CC: Clamping Control (Wild-type DNA),
S1-3: Samples 1-3.
NOTE:
For setup on the Rotor-Gene Q Platforms, the layout must be changed such that the first well contains Positive Control.

When all reagents have been loaded, tightly close the PCR tubes or seal the 96-well plate to prevent evaporation. Spin at 2000 rpm for 1 minute to collect all the reagents. Place in the real-time PCR instrument immediately or store on ice until the instrument is ready.

Instrument Set-Up
Roche LightCycler 96 or RocheLightCycler 480
1. Select New empty experiment>create
2. In the Run Editor>Measurement, choose SYBR Green 1 (470/514) channel on (LC96), SYBR Green 1/HRM Dye on (LC480)
3. Set up run profile using parameters in Table 7. Ramp rates for the LC 96 and LC480 should match settings below.
4. During the analysis set threshold to Auto.

TABLE 4

Roche Light Cycler, LC96 and LC480 Parameters

| Step | Temperature (° C.) | Time (Seconds) | Cycles | Ramp Rate | Mode | Acquisition Mode |
|---|---|---|---|---|---|---|
| PreIncubation | 95 | 300 | 1 | 4.4 | | None |
| Denaturation | 95 | 20 | | 2.2 | Standard | None |
| XNA Annealing | 70 | 40 | X40 | 2.2 | | None |
| Primer Annealing | 64 | 30 | | 2.2 | | None |
| Extension | 72 | 30 | | 1.0 | | Single |
| Melting | 95 | 10 | 1 | 4.4 | | None |
| | 65 | 60 | | 2.2 | | None |
| | 97 | 1 | | 0.20 | | Continuous (5 readings/° C.) |
| Cooling | 37 | 30 | 1 | 2.2 | | None |

* An HRM curve or melt analysis should be run at the end of the PCR reaction. This helps to verify the PCR amplification results and with troubleshooting.

Applied Biosystems Platforms
1. Select File>New Experiment
2. Enter an experiment name and select 7500 (96 wells) or as appropriate
3. Select Quantitation—Standard Curve
4. Select SYBR Green Reagents
5. Select Standard Ramp Rate if available
6. Click on Plate Setup in the left navigation panel
7. Select the Assign Targets and Samples tab and assign samples to the wells
8. Select NONE for the Passive Reference Dye
9. Click on Run Method on the left panel, set reaction volume to 20 ul
10. Setup the cycling parameters as shown in the table below
11. Add Melt Curve at the end of the Cycling Stage. Use continuous and leave default setting for data collection
12. During the analysis set threshold to 0.5 (ABI 7900) and 5000 (ABI 7500).

TABLE 5

Applied Biosystems Platforms Cycling Parameters

| Step | Temperature (° C.) | Time (Seconds) | Cycles | Data Collection |
|---|---|---|---|---|
| PreIncubation | 95 | 300 | 1 | OFF |
| Denaturation | 95 | 20 | X40 | OFF |
| XNA Annealing | 70 | 40 | | OFF |
| Primer Annealing | 66 | 30 | | OFF |
| Extension | 72 | 30 | | ON |
| Melt Curve | Default | | | Continuous |

Rotor-Gene Q Platforms
In the instrument software version 2.1 and above
1. Select File>New, Select Three Step with Melt and click New
2. Select 72-Well Rotor, check the Locking Ring Attached box, click Next
3. Set Reaction volume to 20 ul, click next
4. Set Temperature profile as shown in Table 6.
5. Channel Setup: Select Green Source 470 nm, Detector 510 nm, Gain 7
  a. Click Gain Optimization
  b. Set Temperature to 70 C
  c. Perform Optimization before 1st acquisition
  d. Click optimize acquiring
  e. In the pop-up box enter
    i. Target Sample Range 5 FL up to 10 FL
    ii. Acceptable Gain Range −10 to 10
  f. Click OK, Click Close, Click Next
6. Start-run
7. During the analysis set threshold to Auto.

TABLE 6

Rotor-Gene Q Platforms Cycling Parameters

| Hold | | 95° C. | 5 minutes | X1 | Not Acquiring |
|---|---|---|---|---|---|
| Cycling | Timed Step | 95° C. | 20 seconds | X40 | Not Acquiring |
| | Timed Step | 70° C. | 40 seconds | | Not Acquiring |
| | Timed Step | 64° C. | 30 seconds | | Not Acquiring |
| | Timed Step | 72° C. | 40 seconds | | Acquiring to Cycling A on Green |
| Melt | | Ramp from 65 to 95, rising by 1 degree each step Wait for 90 sec of pre-melt conditioning on first step Wait for 5 seconds for each step afterwards Gain Optimization Check optimize gain before melt on all tubes The gain giving the highest fluorescence less than 95 will be selected. | | | Acquire to melt A on green |

Assessment of Real-Time PCR Results
For the analysis use Absolute Quantitation, automatic baseline. The threshold to be used with each instrument is listed above. Check threshold to ensure that the Threshold is within the exponential growth phase of the amplification plot. If not, the threshold maybe adjusted depending on the run.

The real-time PCR instrument generates a Cq value. Cq is the cycle threshold, the cycle number at which a signal is detected above background fluorescence. The lower the cycle number at which signal rises above background, the stronger the PCR reaction it represents No Template Controls Verify that there is no amplification in no-template controls for each of the reaction mixes. Cq should be undetermined. For some mixes a Cq of 36 or higher may be observed in the NTC. In such cases, check the melting curves obtained. If the melting curve indicates the presence of primer dimers, the reaction may be acceptable. SYBR green binds to primer dimers, resulting in a peak with a lower melting temperature, than the desired amplicon. In many cases formation of primer dimers can be avoided by setting up the PCR reactions on ice, until ready to load into the PCR instrument.

Analysis of Clamping and Positive Controls

The Cq values of the Positive Control (mixed mutant templates) should amplify in the presence of XNAs and yield Cq values given in Table 7.

TABLE 7

Acceptable Cq Ranges for Positive Controls

|  | Positive Control Acceptable Cq Range |
|---|---|
| Ext Control | 20 ≤ Cq ≤ 26 |
| G12 Mix | ≤32 |
| G13 Mix | ≤32 |
| A59 Mix | ≤32 |
| Q61 Mix | ≤30 |
| K117 Mix | ≤34 |
| A146 Mix | ≤30 |

*The Cq value of the Clamping Control (WT DNA) with the Ext Control Mix should be within 20 and 26.
*In addition, the Cq of the Clamping Control with each of the mutation reaction mixes should be at least 3 Cq greater than the Cq of Positive Control with the same reaction mix. If these criteria are not met, the reaction has failed and the results are not valid.
PASS: Cq of Clamping Control with mutation reaction mix - Cq of Positive Control with same mutation reaction mix ≥ 3
FAIL: Cq of Clamping Control with mutation reaction mix - Cq of Positive Control with same mutation reaction mix ≤ 3

Judging Validity of Sample Data Based on External Control Mix Results

The Cq value of the Ext Control Mix can serve as an indication of the purity and the concentration of DNA. Thus, the validity of the test can be decided by the Cq value of the Ext Control Mix. Cq values of any sample with Ext Control Mix should be in the range of 20-27. If the Cq values fall outside the range given in Table 8, the test results should be considered invalid. The experiment should be repeated.

TABLE 8

Acceptable Cq Ranges for Samples with External Control Mix

| Validity | Cq Value of Ext Control Mix | Descriptions and Recommendations |
|---|---|---|
| Optimal | 20 < Cq < 27 | The amplification and amount of DNA sample were optimal. |
| Invalid | Cq ≤ 20 | Possibility of a false positive is high. Repeat the PCR reaction with less DNA. |
| Invalid | Cq ≥ 27 | Not enough DNA or DNA not pure. The amplification is not optimal. Check DNA amount and purity. Repeat the experiment with |

Scoring Mutational Status

IMPORTANT: Refer to the Macro Sheet for QCLAMP™ Cq Mutation Analysis for scoring mutational status. Macro maybe requested by contacting information@diacarta.com If a Cq value is undetermined, assign a Cq of 40 and proceed to analysis.

The table below should be used to determine mutational status

TABLE 9

Scoring Mutational Status

| Mutation |  | G12 | G13 | A59 | Q61 | K117 | A146 |
|---|---|---|---|---|---|---|---|
| Strong Positive: Mutation Content > 5% | Cq | ≤32 | ≤32 | ≤32 | ≤30 | ≤33 | ≤30 |
| Weak Positive: Mutation Content 1-5% | Cq | 32-35* | 32-35* | 30-35* | 30-35* | 33-35* | 30-35* |
|  | ΔCq | ≤10 | ≤9 | ≤8 | ≤8 | ≤10 | ≤8 |
| Negative | Cq | ≥35 | ≥35 | ≤30 | ≥35 | ≥35 | ≥35 |

*If reaction has been set-up with 5 ng of DNA, it is recommended that the experiment be repeated with 10 ng of template DNA to confirm the results.
*Refer to Table 9 for interpretation of A59/Q61 Mutational Status If the Cq value suggests mutation content between 1%-5%, a further calculation of ΔCq should be performed to determine mutational status.
ΔCq = [Cq value of sample with mutant reaction mix] − [Cq value of sample with Ext Control Mix]
For ex: ΔCq = [Cq of sample with G12 mutant reaction mix] − [Cq of sample with Ext Control Mix]

Refer to the table above to confirm mutational status of weak positives.

Differentiating A59/Q61 Mutational Status

The Q61 reaction mix detects both A59 and Q61 mutations, whereas the A59 reaction mix detects only A59 mutations. Therefore, in order to differentiate between A59 and Q61 Mutations a combination of results from the 2 mixes should be used, as described in Table 10 below.

TABLE 10

Interpretation of A59/Q61 Mutational Status

| Reaction Mix | Result Based on Table 12 | Mutational Status |
|---|---|---|
| A59 Reaction Mix | Positive | A59 Mutation |
| Q61 Reaction Mix | Positive |  |
| A59 Reaction Mix | Negative | Q61 Mutation |
| Q61 Reaction Mix | Positive |  |
| A59 Reaction Mix | Negative | Q61 Mutation |
| Q61 Reaction Mix | Positive |  |

HRM Curves as a Tool to Confirm Analyses

In High Resolution Melting Analysis (HRM), the region of interest amplified by PCR is gradually melted. SYBR green is a dsDNA binding dye that is released as the dsDNA amplicon is melted. Emitted fluorescence is measured to generate a characteristic curve. The Tm (Melting Temperature) is characteristic of the GC content, length and sequence of a DNA product and is a useful tool in product identification. The resulting melt profile reflects the mix of amplicons present.

Wild-type DNA (clamping control) is provided. Some amplification may occur in these reactions. Melt profiles of unknown samples should be compared to wild-type and positive controls. Enrichment of one or more peaks, resulting in a melt profile distinct from wild-type DNA profile, can serve as an indication of specific amplification of a mutation target. If the melt profile of an unknown sample is similar to wild-type DNA, and has been scored as a mutation due to Cq, the analysis should be repeated. The resulting PCR product can be sent for Sanger sequencing for further clarification.

HRM curves obtained from unknown samples can be compared to HRM curves obtained from positive controls. Amplicons of similar length and sequence will exhibit the same melt profile.

Example 2

PCR based enrichment of mutant DNA template sequences from template DNA derived from a lung cancer tumor biopsy sample is shown below using a xeno-nucleic acid clamping probe specific for KRAS Exon 2 codon 12. Only codon 12 mutant sequences are amplified as shown by the melting profile of the PCR amplicons generated before enrichment and after XNA clamped PCR enrichment:

The PCR product from the XNA clamped mutant enriched PCR reaction can be isolated and used directly in a Sanger sequencing or Pyrosequencing reaction or else it can be processed for next generation sequencing (NGS) by ligation of adapters and after removal of excess adapters can be used directly for NGS without the need for another PCR amplification step.

Example 3

Multiplex Detection of KRAS Mutations

Figure 3:
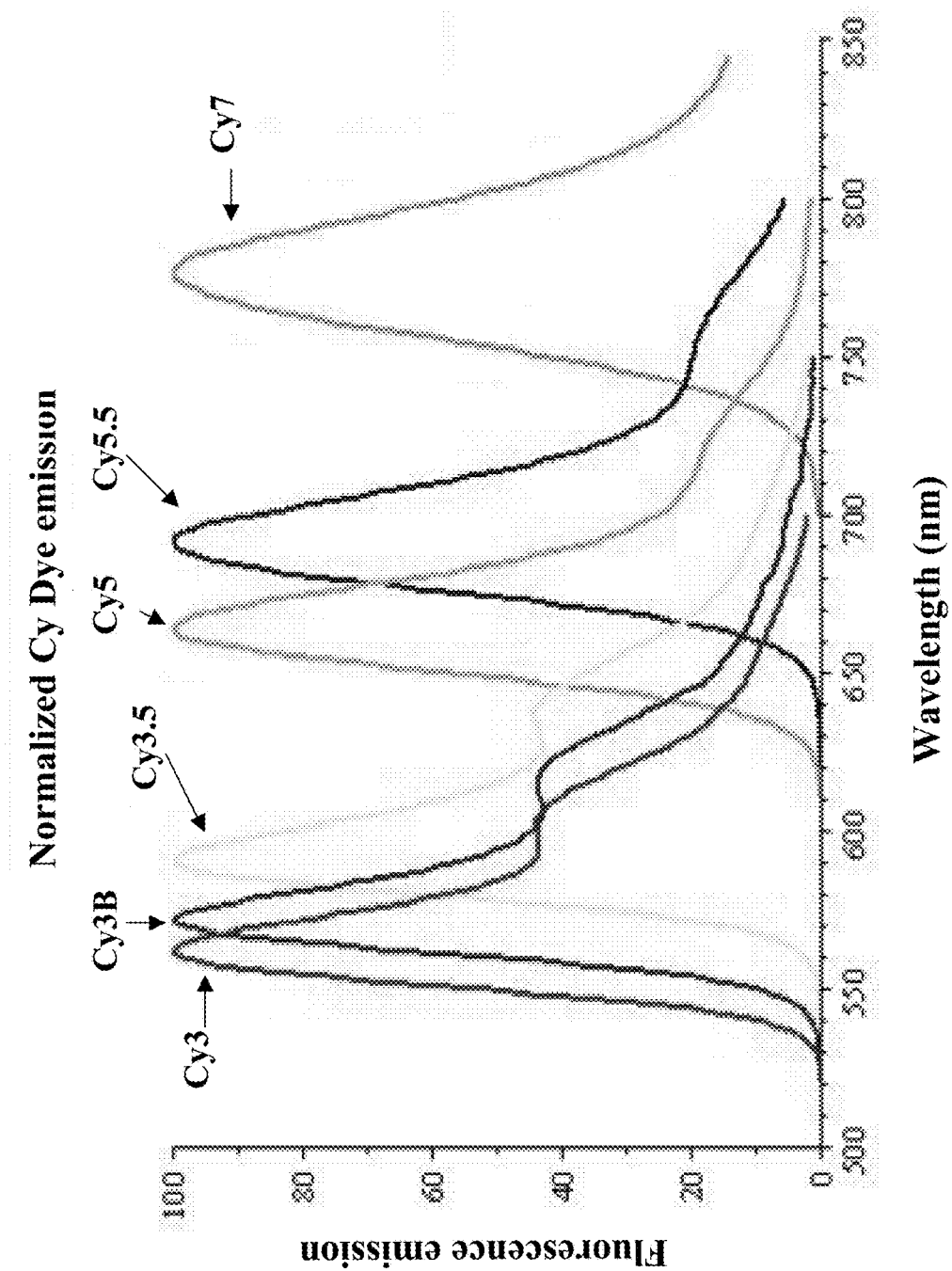
FIG. 3 show specific hydrolysis probe having a different fluorophore (and quencher) selected from the available fluorophores for multiplex applications.

In this example of this invention, locus specific hydrolysis probes are designed to detect mutant amplicons in the KRAS proto-oncogene. Locus specific probes are designed for the following mutant amplicons in KRAS:
Probe 1 KRAS Exon 2 codon 12,
Probe 2 KRAS Exon 2 codon 13,
Probe 3 KRAS Exon 3 codon 59
Probe 4 KRAS Exon3 codon 61,
Probe 5 KRAS Exon 4 codon 117,
Probe 6 KRAS Exon 4 codon 146
and a control probe for a coding sequence in KRAS that has no mutations—Probe 7 KRAS Control probe Each locus specific hydrolysis probe has a different fluorophore (and quencher) selected from the available fluorophores for multiplex applications (see FIGS. 3 and 4).

Figure 5:
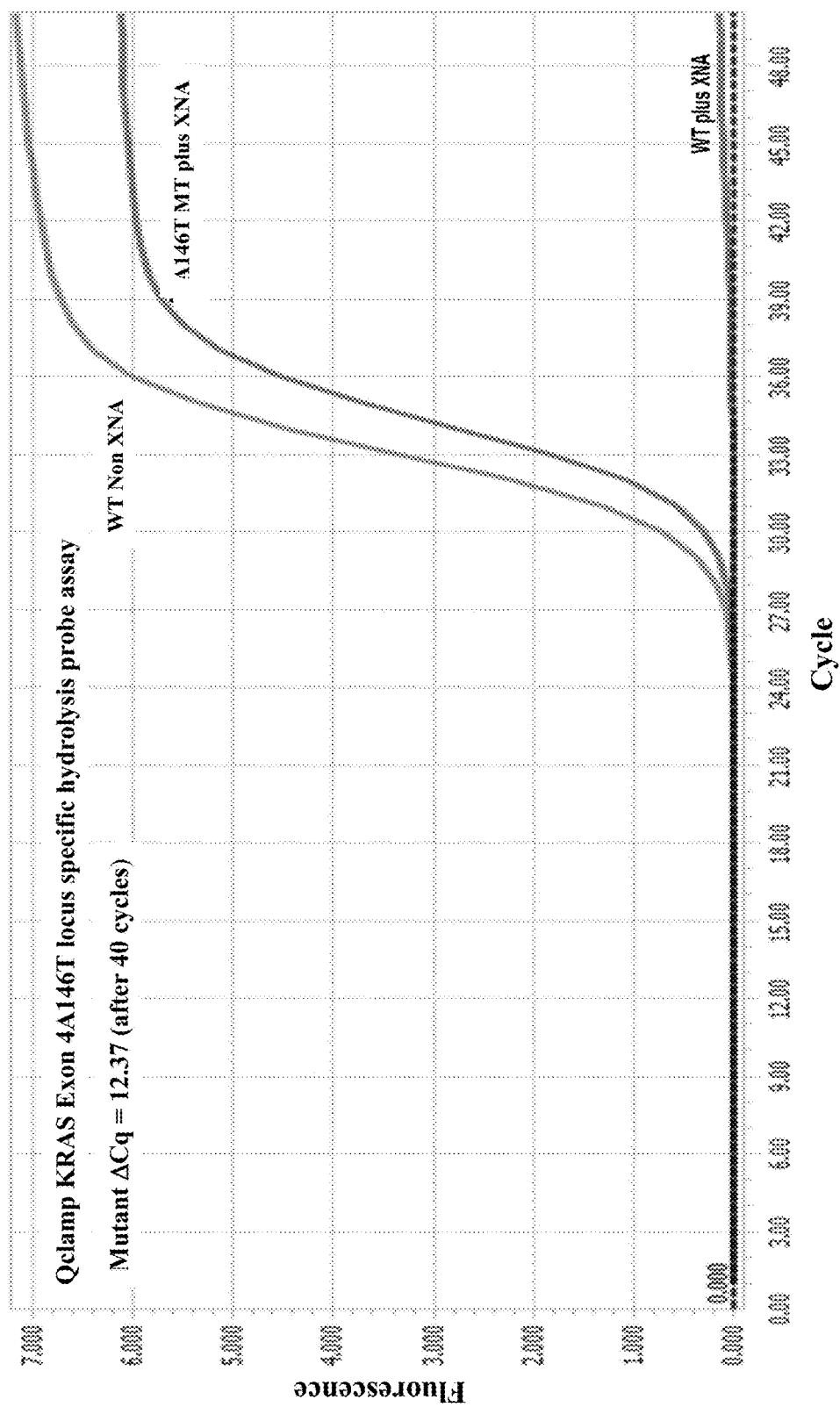
FIG. 5 shows a specific locus specific hydrolysis probe assay.

For the KRAS multiplex assay, KRAS c12, c59, c117 and c146 and KRAS control are detected in a one tube and KRAS c13 and c61 and KRAS control in a separate tube. So that all mutations in the KRAS proto-oncogene can be detected using only 2 PCR reaction tubes. FIG. 5 is an Example of the Exon 4 locus specific probes assay.

Example 4

This example of the invention describes the use of mutation specific capture probes covalently attached to optically bar-coded beads via an amino-linker spacer. Mutant specific probes and control probes for the detection of mutations in KRAS Exon 2 codons 12 and 13 are shown below:

| 1. | G12A | SEQ ID NO: 1 | AGCTGCTGGCGTA |
| --- | --- | --- | --- |
| 2. | G12R | SEQ ID NO: 2 | AGCTCGTGGCGTA |
| 3. | G12D | SEQ ID NO: 3 | AGCTGATGGCGTA |
| 4. | G12C | SEQ ID NO: 4 | AGCTTGTGGCGTA |
| 5. | G12I | SEQ ID NO: 5 | GAGCTATTGGCGT |
| 6. | G12L | SEQ ID NO: 6 | GAGCTCTTGGCGT |
| 7. | G12S | SEQ ID NO: 7 | AGCTAGTGGCGTA |
| 8. | G12V | SEQ ID NO: 8 | AGCTGTTGGCGTA |
| 9. | G13C | SEQ ID NO: 9 | TGGTTGCGTAGGC |
| 10. | G13D | SEQ ID NO: 10 | TGGTGACGTAGGC |
| 11. | G13A | SEQ ID NO: 11 | TGGTGCCGTAGGC |
| 12. | G13V | SEQ ID NO: 12 | TGGTGTCGTAGGC |
| 13. | G13S | SEQ ID NO: 13 | TGGTAGCGTAGGC |
| 14. | G13R | SEQ ID NO: 14 | TGGTCGCGTAGGC |

The control Capture Probes are:

| 15. | (HLA-)DRA Match GGAGACGGTCTGG | SEQ ID NO: 15 |
| --- | --- | --- |
| 16. | (HLA-)DRA Mismatch GGAGACGCTCTGG | SEQ ID NO: 16 |
| 17. | KRAS Wild type: CTGGTGGCGTAGG | SEQ ID NO: 17 |
| 18. | KRAS PCR control AAGGCCTGCTGAA | SEQ ID NO: 18 |

All probes contain a 5'-amino-linker for bar-coded bead conjugation. After, performing XNA clamping PCR reaction is done to eliminate wild-type KRAS using the following primers: KRAS Exon 2 Forward: SEQ ID NO: 19 5'-GTACTGGTGGAGTATTTGATAG TG-3', KRAS Exon 2 Reverse: SEQ ID NO: 20 5'-ATCGTCAAGGCACTCTT GCCTAC-3' and XNA Clamp Probe Blocker specific for KRAS Exon 2 12/13 optically bar-coded mutation specific capture beads are added and incubated for hybridization capture. After washing detection is performed with Streptavidin Phycoerythrin (SAPE) and measured on DigiPlex analyzer.

Example 5

QCLAMP™ Sample DNA Preparation Protocol

Genomic DNA should be obtained either from whole blood, cells, purified peripheral blood lymphocytes of whole blood, polynuclear cells, or granulocytes, tissue biopsies or FFPE sections. For comparable results it is recommended that the same cellular fraction and DNA extraction method are used. DNA extraction can be performed using a home-brew method or a commercially available kit.

Carefully transfer FFPE section(s) or equivalent amount of fresh tissue, cells (100 to 100,000 cells) or 200 µl whole blood to a clean 1.7 ml polypropylene micro-centrifuge tube and add the required volume of lysis solution. For FFPE sections add 50 µL of lysis Solution. For liquid or moist cells or tissues add 2× volume of the sample volume.

For FFPE samples warm each sample in heating block at 95° C. until paraffin melts and then vortex each warm sample for 10 seconds. Return the sealed sample preparation tubes to the heating block and heat at 95° C. for 20 minutes make sure to carefully remove the tubes every 5 min and vortex each tube for 10 s and return to heating block.

Remove sample preparation tube from heating block and immediately add an equivalent volume of lysis solution as the volume added of lysis solution from step 1 above. For example, if 50 μL of lysis solution was added, add 50 μL of lysis solution.

Vortex each sample for 10 seconds. Spin down the sample preparation tubes in a microcentrifuge and allow to cool. Use the resultant lysis solution lysate supernatant directly in the PCR reaction.

The extracted DNA needs to be diluted to a concentration of 5 ng/μl in 1× TE buffer at pH 8.0 and then stored at +4 to +8° C. for 1 week or at −20° C. if longer term storage is required. The QCLAMP™ qPCR reaction is optimized for DNA samples containing 5-20 ng of purified genomic DNA.

The sequences in the Table below show exemplary primers and xeno and peptide nucleic acids.

| Sequence Name | | |
|---|---|---|
| 1047SSF001NEW | SEQ ID NO: 21 | CGAAAGACCCTAGCCTTAGATAAAACT |
| 1047SSR001NEW | SEQ ID NO: 22 | ATTGTGTGGAAGATCCAATCCATTT |
| 146R002f | SEQ ID NO: 23 | ACGTTGGATGTGTACCATACCTGTCTGGTCTT |
| 21FW1S | SEQ ID NO: 24 | GTTTTCCCAGTCACGACACGTTGGATGCAGCCAGGAACGTACTGGTGA |
| BIOBRAFCONTRLFP | SEQ ID NO: 25 | /5Biosg/CTCCAGATCTCAGTAAGGTACGG |
| BIOKRASCONTRLFP | SEQ ID NO: 26 | /5Biosg/TGAGGGAGATCCGACAATACAG |
| BRAFAZFPNEW02 | SEQ ID NO: 27 | ACAGTAAAAATAGGTGATTTTGGTCTAGCTA |
| BRAFAZFPNew02s | SEQ ID NO: 28 | GTTTTCCCAGTCACGACACGTTGGATGACAGTAAAAATAGGTGATTTTGGTCTAGCTA |
| BRAFAZRP001 | SEQ ID NO: 29 | CATCCACAAAATGGATCCAGACAA |
| BRAFAZRP001s | SEQ ID NO: 30 | CAGGAAACAGCTATGACACGTTGGATGCATCCACAAAATGGATCCAGACAA |
| BRAFCONTRLFP | SEQ ID NO: 31 | CTCCAGATCTCAGTAAGGTACGG |
| BRAFCONTRLRP | SEQ ID NO: 32 | GGGAAAGAGTGGTCTCTCATC |
| C790F002f | SEQ ID NO: 33 | ACGTTGGATGTCCACCGTGCAGCTCATC |
| C790F002fS | SEQ ID NO: 34 | GTTTTCCCAGTCACGACACGTTGGATGTCCACCGTGCAGCT |
| C790R001Bf | SEQ ID NO: 35 | ACGTTGGATGGTCTTTGTGTTCCCGGACAT |
| C790R001BfS | SEQ ID NO: 36 | CAGGAAACAGCTATGACACGTTGGATGGTCTTTGTGTTCCC |
| Ex19NewFS | SEQ ID NO: 37 | GTTTTCCCAGTCACGACACGTTGGATGCTCTCTGTCATAGGGACTCTGGATCC |
| Ex19NewFwd | SEQ ID NO: 38 | CTCTCTGTCATAGGGACTCTGGATCC |
| Ex19NewRev | SEQ ID NO: 39 | AGCAAAGCAGAAACTCACATCGAG |
| Ex19NewRS | SEQ ID NO: 40 | CAGGAAACAGCTATGACACGTTGGATGAGCAAAGCAGAAACTCACATCGAG |
| Exon18NewFS | SEQ ID NO: 41 | GTTTTCCCAGTCACGACACGTTGGATGGCTCCCAACCAAGCTCTCTTGA |
| Exon18NewFwd | SEQ ID NO: 42 | GCTCCCAACCAAGCTCTCTTGA |
| Exon18NewRev | SEQ ID NO: 43 | CTGTGCCAGGGACCTTACCTTATAC |
| Exon18NewRS | SEQ ID NO: 44 | CAGGAAACAGCTATGACACGTTGGATGCTGTGCCAGGGACCTTACCTTATAC |
| Exon2FowardNew | SEQ ID NO: 45 | TTTGCCAAGGCACGAGTAACAAG |
| Exon2ReverseNew | SEQ ID NO: 46 | CCCAAGGACCACCTCACAGTTAT |
| JAK2XN9F001 | SEQ ID NO: 47 | TTAACTGCAGATGCACATCATTACCT |
| KRAS117F002 | SEQ ID NO: 48 | GGACTCTGAAGATGTACCTATGG |

-continued

| Sequence Name | | |
|---|---|---|
| KRAS117F002s | SEQ ID NO: 49 | GTTTTCCCAGTCACGACACGTTGGATGGGACTCTGAAGATGTACCTATGG |
| KRAS117R002 | SEQ ID NO: 50 | GCTAAGTCCTGAGCCTGTTT |
| KRAS117R002s | SEQ ID NO: 51 | CAGGAAACAGCTATGACACGTTGGATGGCTAAGTCCTGAGCCTGTTT |
| KRAS146F003 | SEQ ID NO: 52 | ACACAAAACAGGCTCAGGAC |
| KRAS146F003s | SEQ ID NO: 53 | GTTTTCCCAGTCACGACACGTTGGATGACACAAAACAGGCTCAGGAC |
| KRAS146R002 | SEQ ID NO: 54 | CAGTGTTACTTACCTGTCTTGTCTT |
| KRAS146R002s | SEQ ID NO: 55 | CAGGAAACAGCTATGACACGTTGGATGCAGTGTTACTTACCTGTCTTGTCTT |
| KRASBIOFP002 | SEQ ID NO: 56 | AAGGCCTGCTGAAAATGACTG |
| KRASBioFP002s | SEQ ID NO: 57 | GTTTTCCCAGTCACGACACGTTGGATGAAGGCCTGCTGAAAATGACTG |
| KRASC12RP002s | SEQ ID NO: 58 | CAGGAAACAGCTATGACACGTTGGATGTCAAGGCACTCTTGCCTACGC |
| KRASc13F001 | SEQ ID NO: 59 | ACTTGTGGTAGTTGGAGCTGGT |
| KRASC13F001s | SEQ ID NO: 60 | GTTTTCCCAGTCACGACACGTTGGATGACTTGTGGTAGTTGGAGCTGGT |
| KRASC13NEWR001 | SEQ ID NO: 61 | TCATGAAAATGGTCAGAGAAACCTT |
| KRASC13NewR001s | SEQ ID NO: 62 | CAGGAAACAGCTATGACACGTTGGATGACTTGTGGTAGTTGGAGCTGGT |
| KRASC59R001 | SEQ ID NO: 63 | ATTGCACTGTACTCCTCTTGACC |
| KRASC59R001s | SEQ ID NO: 64 | CAGGAAACAGCTATGACACGTTGGATGATTGCACTGTACTCCTCTTGACC |
| KRASc61F001 | SEQ ID NO: 65 | CTCTTGGATATTCTCGACACAGCAGGT |
| KRASC61F001s | SEQ ID NO: 66 | GTTTTCCCAGTCACGACACGTTGGATGCTCTTGGATATTCTCGACACAGCAGGT |
| KRASc61F003 | SEQ ID NO: 67 | CCAGACTGTGTTTCTCCCTT |
| KRASC61F003s | SEQ ID NO: 68 | GTTTTCCCAGTCACGACACGTTGGATGCCAGACTGTGTTTCTCCCTT |
| KRASCONTRLFP | SEQ ID NO: 69 | TGAGGGAGATCCGACAATACAG |
| KRASCONTRLRP | SEQ ID NO: 70 | TCTGCCAAAATTAATGTGCTGAACT |
| L858RBR001 | SEQ ID NO: 71 | TTCTCTTCCGCACCCAGC |
| L858RBR001S | SEQ ID NO: 72 | CAGGAAACAGCTATGACACGTTGGATGTTCTCTTCCGCACCCAGC |
| L858RNewFS | SEQ ID NO: 73 | GTTTTCCCAGTCACGACACGTTGGATGTGAAAACACCGCAGCATGTCAAGA |
| L858RNewFwd | SEQ ID NO: 74 | TGAAAACACCGCAGCATGTCAAGA |
| L858RNewRev | SEQ ID NO: 75 | CCTTACTTTGCCTCCTTCTGCATG |
| L858RNewRS | SEQ ID NO: 76 | CAGGAAACAGCTATGACACGTTGGATGCCTTACTTTGCCTCCTTCTGCATG |
| NC12FP004 | SEQ ID NO: 77 | TGGTGGGATCATATTCATCTACAAAG |
| NC12FP004_G13_RevS | SEQ ID NO: 78 | TGGTGGGATCATATTCATCTACAAAG |
| NC12FP004s | SEQ ID NO: 79 | CAGGAAACAGCTATGACACGTTGGATGTGGTGGGATCATATTCATCTACAAAG |

-continued

| Sequence Name | | |
|---|---|---|
| NRAS117F001 | SEQ ID NO: 80 | AGTAAAAGACTCGGATGATGTACCTAT |
| NRAS117F002f | SEQ ID NO: 81 | ACGTTGGATGACCTATGGTGCTAGTGGGAAAC |
| NRAS117F003 | SEQ ID NO: 82 | ACGTTGGATGTCCCGTTTTTAGGGAGCAGA |
| NRAS117F004 | SEQ ID NO: 83 | CCCGTTTTTAGGGAGCAGAT |
| NRAS117R002 | SEQ ID NO: 84 | CAGTTCGTGGGCTTGTTTTG |
| NRAS117R004 | SEQ ID NO: 85 | CTTGCACAAATGCTGAAAGC |
| NRASc12F001 | SEQ ID NO: 86 | AAACTGGTGGTGGTTGGAGCA |
| NRASC12F001s | SEQ ID NO: 87 | GTTTTCCCAGTCACGACACGTTGGATGAAACTGGTGGTGGTTGGAGCA |
| NRASC13F001 | SEQ ID NO: 88 | GGTGGTGGTTGGAGCAGGT |
| NRASC13F001s | SEQ ID NO: 89 | GTTTTCCCAGTCACGACACGTTGGATGGGTGGTGGTTGGAGCAGGT |
| NRASC59F001 | SEQ ID NO: 90 | ACACCCCCAGGATTCTTACAGA |
| NRASC59F001s | SEQ ID NO: 91 | GTTTTCCCAGTCACGACACGTTGGATGACACCCCCAGGATTCTTACAGA |
| NRASC59R001 | SEQ ID NO: 92 | ATGGCACTGTACTCTTCTTGTCC |
| NRASC59R001s | SEQ ID NO: 93 | CAGGAAACAGCTATGACACGTTGGATGATGGCACTGTACTCTTCTTGTCC |
| NRASc61F001 | SEQ ID NO: 94 | GTTGGACATACTGGATACAGCTGGA |
| NRASC61F001s | SEQ ID NO: 95 | GTTTTCCCAGTCACGACACGTTGGATGGTTGGACATACTGGATACAGCTGGA |
| NRASXN3REVSet4 | SEQ ID NO: 96 | CCGCAAATGACTTGCTATTA |
| NRASXN3RevSet4s | SEQ ID NO: 97 | CAGGAAACAGCTATGACACGTTGGATGCCGCAAATGACTTGCTATTA |
| NRASXN5FwSet1 | SEQ ID NO: 98 | ACACACTGGTAAGAGAAATAC |
| NRASXN5REVSet1 | SEQ ID NO: 99 | CTGAGTCCCATCATCACT |
| BR001 | SEQ ID NO: 100 | ATCGAGATTTCACTGTAGCTAGAC |
| DPCA001 | SEQ ID NO: 101 | ACTTCAGGCAGCGTCTTCA |
| DPCA002 | SEQ ID NO: 102 | TGTTCAGAGCACACTTCAG |
| DPCA003 | SEQ ID NO: 103 | CTGGTGGTTGAATTTGCTG |
| DPCA004 | SEQ ID NO: 104 | CATGAGCTCCAGCAGGATGAAC |
| DPCA005 | SEQ ID NO: 105 | CCGAAGTCTCCAATCTTGG |
| DPCA006 | SEQ ID NO: 106 | TAGATGTCTCGGGCCATCC |
| DPCBRC001 | SEQ ID NO: 107 | GGGACACTCTAAGAT |
| DPCBRC002 | SEQ ID NO: 108 | TTCTGTCCTGGGATTCTC |
| DPCBRC003 | SEQ ID NO: 109 | AGATTTTCCACTTGCTGT |
| DPCBRCA001-2 | SEQ ID NO: 110 | CCAGATGGGACACTCTAAGATTTTC |
| DPCBRCA002-2 | SEQ ID NO: 111 | CCTTTCTGTCCTGGGATTCTCTT |
| DPCBRCA003-2 | SEQ ID NO: 112 | GACAGATTTTCCACTTGCTGTGCTAA |
| DPCBRCA004 | SEQ ID NO: 113 | CATAAAGGACACTGTGAAGGCC |
| DPCBRCA004B | SEQ ID NO: 114 | D-LYS-O-GGCCTTCACAGTGTCCTTTATG |

-continued

| Sequence Name | | |
|---|---|---|
| DPCCKT002 | SEQ ID NO: 115 | D-LYS-O-CATTCTTGATGTCTCTGGCTAG |
| DPCE001 | SEQ ID NO: 116 | GAGCCCAGCACTTT |
| DPCE001B | SEQ ID NO: 117 | D-LYS-O-CGGAGCCCAGCACTTTGAT |
| DPCE001B1 | SEQ ID NO: 118 | D-LYS-O-CGGAGCCCAGCACTTTGAT |
| DPCE002 | SEQ ID NO: 119 | NH(2)-AGATGTTGCTTCTCTTAA-CONH(2) |
| DPCE002B | SEQ ID NO: 120 | D-LYS-O-AGATGTTGCTTCTCTTAA |
| DPCE002C | SEQ ID NO: 121 | D-LYS-O-CGGAGATGTTGCTTCTCTTAATTCC |
| DPCE004 | SEQ ID NO: 122 | CAGTTTGGCCAGCCCA |
| DPCE004B | SEQ ID NO: 123 | CAGTTTGGCCAGCCCA-O-D-LYS |
| DPCE004C | SEQ ID NO: 124 | D-LYS-O-TTTGGCCAGCCCAAAATCTGT |
| DPCE004D | SEQ ID NO: 125 | D-LYS-O-GGCCAGCCCAAAATCTGT |
| DPCE005 | SEQ ID NO: 126 | ACCCAGCAGTTTGGC |
| DPCE005B | SEQ ID NO: 127 | D-LYS-O-ACCCAGCAGTTTGGC |
| DPCE006 | SEQ ID NO: 128 | GCTGCGTGATGAG |
| DPCE007 | SEQ ID NO: 129 | GCTGCGTGATGA |
| DPCE008 | SEQ ID NO: 130 | AGCTCATCACGCAGCTCATG |
| DPCE008B | SEQ ID NO: 131 | D-LYS-O-CAGCTCATCACGCAGCTCATGC |
| DPCE008C | SEQ ID NO: 132 | D-LYS-O-TCATCACGCAGCTCATGCCCTT |
| DPCE008D | SEQ ID NO: 133 | D-LYS-O-CTCATCACGCAGCTCATG |
| DPCE008E | SEQ ID NO: 134 | D-LYS-O-TGAGCTGCGTGATG |
| DPCE009B | SEQ ID NO: 135 | D-LYS-O-TCCACGCTGGCCATCACGTA |
| DPCE009B-1 | SEQ ID NO: 136 | TCCACGCTGGCCATCACGTA-O-D-LYS |
| DPCE010B | SEQ ID NO: 137 | TGGGGGTTGTCCAC-O-D-LYS |
| DPCE011 | SEQ ID NO: 138 | GCACACGTGGGGGTT-O-D-LYS |
| DPCE012 | SEQ ID NO: 139 | D-LYS-O-ACAACCCCCACGTGTGC |
| DPCH001 | SEQ ID NO: 140 | CTGAGCCAGGAGAAAC |
| DPCH002 | SEQ ID NO: 141 | GTAAACTGAGCCAGGAG |
| DPCH003 | SEQ ID NO: 142 | ATGGCACTAGTAAACTGAGC |
| DPCH004 | SEQ ID NO: 143 | ATCCATATAACTGAAAGCCAA |
| DPCH005 | SEQ ID NO: 144 | ACCACATCATCCATATAACTGAA |
| DPCHRAS001B | SEQ ID NO: 145 | D-LYS-O-O-TTGCCCACACCGCCGGC |
| DPCHRAS002 | SEQ ID NO: 146 | D-LYS-O-O-TCTTGCCCACACCGCC |
| DPCHRAS003 | SEQ ID NO: 147 | D-LYS-O-O-TACTCCTCCTGGCCGGC |
| DPCJ001 | SEQ ID NO: 148 | CGTCTCCACAGACACATACTCCA |
| DPCJ002B | SEQ ID NO: 149 | CGTCTCCACAGACACATACTCCA-O-D-LYS |
| DPCK001B | SEQ ID NO: 150 | GCCTACGCCACCAGCTCCAAC-O-D-LYS |
| DPCK001B2 | SEQ ID NO: 151 | GCCTACGCCACCAGCTCCAAC-O-O-D-LYS |
| DPCK001C | SEQ ID NO: 152 | CTACGCCACCAGCTCCAACTACCA |
| DPCK001C2 | SEQ ID NO: 153 | CTACGCCACCAGCTCCAACTACCA-O-D-LYS |

-continued

| Sequence Name | | |
|---|---|---|
| DPCK002 | SEQ ID NO: 154 | TCTTGCCTACGCCACCAGCTCCA |
| DPCK003 | SEQ ID NO: 155 | TGTACTCCTCTTGACCTGCTGTG |
| DPCK003B | SEQ ID NO: 156 | D-LYS-O-TGTACTCCTCTTGACCTGCTGTG |
| DPCK004 | SEQ ID NO: 157 | NH(2)-GGCAAATCACATTTATTTCCTAC-CONH(2) |
| DPCK004B | SEQ ID NO: 158 | D-LYS-O-GGCAAATCACATTTATTTCCTAC |
| DPCK005B | SEQ ID NO: 159 | D-LYS-O-TGTCTTGTCTTTGCTGATGTTTC |
| DPCK005 | SEQ ID NO: 160 | TGTCTTGTCTTTGCTGATGTTTC |
| DPCK005C | SEQ ID NO: 161 | D-LYS-O-TGTCTTGTCTTTGCTGATGTTTC |
| DPCK006 | SEQ ID NO: 162 | NH(2)-CTCTTGACCTGCTGTGTCGAG-CONH(2) |
| DPCN001 | SEQ ID NO: 163 | TCCCAACACCACCTGCTCCAA |
| DPCN001B | SEQ ID NO: 164 | D-LYS-O-CAACACCACCTGCTCCAACCACCAC |
| DPCN002 | SEQ ID NO: 165 | CTTTTCCCAACACCACCTGCTCC |
| DPCN002B | SEQ ID NO: 166 | D-LYS-O-TGCGCTTTTCCCAACACCACCTGCT |
| DPCN003B | SEQ ID NO: 167 | GGCACTGTACTCTTCTTGTCCAG |
| DPCN004B | SEQ ID NO: 168 | D-LYS-O-TCTGGTCTTGGCTGAGGTTTC |
| DPCN006 | SEQ ID NO: 169 | NH(2)-GGCAAATCACACTTGTTTCCCAC-CONH(2) |
| DPCN006B | SEQ ID NO: 170 | D-LYS-O-GGCAAATCACACTTGTTTCCCAC |
| DPCN007 | SEQ ID NO: 171 | NH(2)-TTCTTGTCCAGCTGTATCCAGTATG-CONH(2) |
| DPCPKA003B | SEQ ID NO: 172 | D-LYS-O-AGATCCTCTCTGAAATCAC |
| DPCPKA004 | SEQ ID NO: 173 | D-LYS-O-TCTTTCTCCTGCTCAGTGATTTCA |
| DPCPKA005 | SEQ ID NO: 174 | D-LYS-O-AATGATGCACATCATGGTGGCTG |
| NRASN003C | SEQ ID NO: 175 | D-LYS-O-GGCACTGTACTCTTCTTGTCCAG |
| QMDXNA001 | SEQ ID NO: 176 | NH(2)-O-TTCATCAACCGCACTCTGTTTATCTC |
| QMDXNA002 | SEQ ID NO: 177 | NH(2)-O-TGGCGACGACAATGGACCCAATTAT |
| QMDXNA003 | SEQ ID NO: 178 | NH(2)-O-AGATGTAGTTAGCAATCGGTCCTTGTTGTA |
| QMDXNA004 | SEQ ID NO: 179 | NH(2)-O-GGGTAATTGAGGTAACGTAGGTATCAAGAT |
| QMDXNA005 | SEQ ID NO: 180 | NH(2)-O-TACTATCGACTGACATGAGGCTTGTGT |
| XNADE001 | SEQ ID NO: 181 | D-LYS-O-AGTCCGACGATCTGGAATTC |
| XNADE002 | SEQ ID NO: 182 | D-LYS-O-ACTGGAGTTCAGACGTGTG |
| XNADE003 | SEQ ID NO: 183 | D-LYS-O-CTCTTCCGATCAGATCGGAA |
| XNADE003b | SEQ ID NO: 184 | D-LYS-O-CTCTTCCGATCAGATCGGAAG |
| XNAFGFR001 | SEQ ID NO: 185 | D-LYS-O-O-AGCGCTCCCCGCACC |
| XNAFGFR001 | SEQ ID NO: 186 | D-LYS-O-O-AGCGCTCCCCGCACC |
| XNAFGFR002 | SEQ ID NO: 187 | D-LYS-O-GGGGAGCGCTCTGT-O-TTTTT |
| XNAFGFR003 | SEQ ID NO: 188 | D-LYS-O-O-AGCGCTCCCCGCACC-O-TTTTTT |
| XNAFGFR004 | SEQ ID NO: 189 | D-LYS-O-TGCATACACACTGCCCGCCT |

Other sequences of interest in connection with the invention include the following exons:

BRAF Ex 15 NCBI NG_007873.3; DNA; Wildtype
SEQ ID NO. 190
TAGAAATTAG ATCTCTTACC TAAACTCTTC ATAATGCTTG CTCTGATAGG AAAATGAGAT

CTACTGTTTT CCTTTACTTA CTACACCTCA GATATATTTC TTCATGAAGA CCTCACAGTA

AAAATAGGTG ATTTTGGTCT AGCTACAGTG AAATCTCGAT GGAGTGGGTC CCATCAGTTT

GAACAGTTGT CTGGATCCAT TTTGTGGATG GTAAGAATTG AGGCTATTTT TCCACTGATT

AAATTTTTGG CCCTGAGATG CTGCTGAGTT ACTAGAAAGT CATTGAAGGT CTCAACTATA

GTATTTTCAT AGTTCCCAGT ATTCACAAAA ATCAGTGTTC TTATTTTTTA TGTAAATAGA

EGFR Ex18 GeneGenBank: AF288738.1 NCBI NM_005228.3; DNA; Wildtype
SEQ ID NO. 191
TAGAGAAGGC GTACATTTGT CCTTCCAAAT GAGCTGGCAA GTGCCGTGTC CTGGCACCCA

AGCCCATGCC GTGGCTGCTG GTCCCCCTGC TGGGCCATGT CTGGCACTGC TTTCCAGCAT

GGTGAGGGCT GAGGTGACCC TTGTCTCTGT GTTCTTGTCC CCCCCAGCTT GTGGAGCCTC

TTACACCCAG TGGAGAAGCT CCCAACCAAG CTCTCTTGAG GATCTTGAAG GAAACTGAAT

TCAAAAAGAT CAAAGTGCTG GGCTCCGGTG CGTTCGGCAC GGTGTATAAG GTAAGGTCCC

TGGCACAGGC CTCTGGGCTG GGCCGCAGGG CCTCTCATGG TCTGGTGGGG AGCCCAGAGT

CCTTGCAAGC TGTATATTTC CATCATCTAC TTTACTCTTT GTTTCACTGA GTGTTTGGGA

AACTCCAGTG TTTTTCCCAA GTTATTGAGA GGAAATCTTT TATAACCACA GTAATCAGTG

EGFR Ex19 GeneGenBank: AF288738.1 NCBI NM_005228.3; DNA; Wildtype
SEQ ID NO. 192
AGCCCAACAG CTGCAGGGCT GCGGGGGCGT CACAGCCCCC AGCAATATCA GCCTTAGGTG

CGGCTCCACA GCCCCAGTGT CCCTCACCTT CGGGGTGCAT CGCTGGTAAC ATCCACCCAG

ATCACTGGGC AGCATGTGGC ACCATCTCAC AATTGCCAGT TAACGTCTTC CTTCTCTCTC

TGTCATAGGG ACTCTGGATC CCAGAAGGTG AGAAAGTTAA AATTCCCGTC GCTATCAAGG

AATTAAGAGA AGCAACATCT CCGAAAGCCA ACAAGGAAAT CCTCGATGTG AGTTTCTGCT

TTGCTGTGTG GGGGTCCATG GCTCTGAACC TCAGGCCCAC CTTTTCTCAT GTCTGGCAGC

TGCTCTGCTC TAGACCCTGC TCATCTCCAC ATCCTAAATG TTCACTTTCT ATGTCTTTCC

EGFR Ex20 GeneGenBank: AF288738.1 NCBI NM_005228.3; DNA; Wildtype
SEQ ID NO. 193
AAAATTCCCG TCGCTATCAA GGAATTAAGA GAAGCAACAT CTCCGAAAGC CAACAAGGAA

ATCCTCGATG AAGCCTACGT GATGGCCAGC GTGGACAACC CCCACGTGTG CCGCCTGCTG

GGCATCTGCC TCACCTCCAC CGTGCAGCTCATCACGCAGC TCATGCCCTT CGGCTGCCTC

CTGGACTATG TCCGGGAACA CAAAGACAAT ATTGGCTCCC AGTACCTGCT CAACTGGTGT

GTGCAGATCG CAAAGGGCAT GAACTACTTG GAGGACCGTC GCTTGGTGCA CCGCGACCTG

GCAGCCAGGA ACGTACTGGT GAAAACACCG CAGCATGTCA AGATCACAGA TTTTGGGCTG

GCCAAACTGC TGGGTGCGGA AGAGAAAGAA TACCATGCAG AAGGAGGCAA AGTGCCTATC

AAGTGGATGG CATTGGAATC AATTTTACAC AGAATCTATA CCCACCAGAG TGATGTCTGG

EGFR Ex21 GeneGenBank: AF288738.1 NCBI NM_005228.3; DNA; Wildtyp
SEQ ID NO. 194
GGCATCTGCC TCACCTCCAC CGTGCAGCTC ATCACGCAGC TCATGCCCTT CGGCTGCCTC

CTGGACTATG TCCGGGAACA CAAAGACAAT ATTGGCTCCC AGTACCTGCT CAACTGGTGT

GTGCAGATCG CAAAGGGCAT GAACTACTTG GAGGACCGTC GCTTGGTGCA CCGCGACCTG

```
GCAGCCAGGA ACGTACTGGT GAAAACACCG CAGCATGTCA AGATCACAGA TTTTGGGCTG

GCCAAACTGC TGGGTGCGGA AGAGAAAGAA TACCATGCAG AAGGAGGCAA AGTGCCTATC

AAGTGGATGG CATTGGAATC AATTTTACAC AGAATCTATA CCCACCAGAG TGATGTCTGG

AGCTACGGGG TGACCGTTTG GGAGTTGATG ACCTTTGGAT CCAAGCCATA TGACGGAATC
```

HRAS Ex3 NCBI Reference Sequence: NG_007666.1;
DNA; Wildtype
SEQ ID NO. 195
```
CTGCAGGATT CCTACCGGAA GCAGGTGGTC ATTGATGGGG AGACGTGCCT GTTGGACATC

CTGGATACCG CCGGCCAGGA GGAGTACAGC GCCATGCGGG ACCAGTACAT GCGCACCGGG

GAGGGCTTCC TGTGTGTGTT TGCCATCAAC AACACCAAGT CTTTTGAGGA CATCCACCAG

TACAGGTGAA CCCCGTGAGG CTGGCCCGGG AGCCCACGCC GCACAGGTGG GGCCAGGCC
```

JAK2 NCBI Reference Sequence: NG_009904.1;
DNA; wildtype
SEQ ID NO. 196
```
CTGACATCTACCTCTAGTTGTACTTCTGTCCTCTATTTCAGGTGTTATGGGTCAAGCCTGTTTGACTGGC

ATTATTCATGATTCCTGTACCACTCTTGCTCTCTCTCACTTTGATCTCCATATTCCAGGCTTACACAGGG

GTTTCCTCAGAACGTTGATGGCAGTTGCAGGTCCATATAAAGGGACCAAAGCACATTGTATCCTCATC

TAGTCATGCTGAAAGTAGGAGAAAGTGCATCTTTATTATGGCAGAGAGAATTTTCTGAACTATTTATG

GACAACAGTCAAACAACAATTCTTTGTACTTTTTTTTTCCTTAGTCTTTCTTTGAAGCAGCAAGTATGA

TGAGCAAGCTTTCTCACAAGCATTTGGTTTTAAATTATGGAGTATGTGTCTGTGGAGACGAGAGTAAG

TAAAACTACAGGCTTTCTAATGCCTTTCTCAGAGCATCTGTTTTTGTTTATATAGAAAATTCAGTTTCAG

GATCACAGCTAGGTGTCAGTGTAAACTATAATTTAACAGGAGTTAAGTATTTTTGAAACTGAAAACAC

TGTAGGACTATTCAGTTATATCTTGTGAAAAAGGAAAGCAATGAAGTTAAAAGTAGAAGGTTACAATG

CCCAAACAATAGAGTATTATAGTAAACAAATGTCTATAAAACATTTTGTGTTCATGATAGCAAAAGAG

ATTATGGCAGGTTCAACATAACATTGGAATAACTGGCCTTTTCAGTACAAACTTATCTGGAATTATGAA

GACAAAGCATA
```

KRAS Ex2 NCBI Reference Sequence: NG_007524.1;
DNA; wildtype
SEQ ID NO. 197
```
GGTACTGGTG GAGTATTTGA TAGTGTATTA ACCTTATGTG TGACATGTTC TAATATAGTC

ACATTTTCAT TATTTTTATT ATAAGGCCTG CTGAAAATGA CTGAATATAA ACTTGTGGTA

GTTGGAGCTG GTGGCGTAGG CAAGAGTGCC TTGACGATAC AGCTAATTCA GAATCATTTT

GTGGACGAAT ATGATCCAAC AATAGAGGTA AATCTTGTTT TAATATGCAT ATTACTGGTG
```

KRAS Ex3 NCBI Reference Sequence: NG_007524.1;
DNA; wildtype
SEQ ID NO. 198
```
CTTCTCAGGA TTCCTACAGG AAGCAAGTAG TAATTGATGG AGAAACCTGT CTCTTGGATA

TTCTCGACAC AGCAGGTCAA GAGGAGTACA GTGCAATGAG GGACCAGTAC ATGAGGACTG

GGGAGGGCTT TCTTTGTGTA TTTGCCATAA ATAATACTAA ATCATTTGAA GATATTCACC

ATTATAGGTG GGTTTAAATT GAATATAATA AGCTGACATT AAGGAGTAAT TATAGTTTTT
```

KRAS Ex4 NCBI Reference Sequence: NG_007524.1;
DNA; wildtype
SEQ ID NO. 199
```
GTGCTATAAC TTTTTTTTCT TTCCCAGAGA ACAAATTAAA AGAGTTAAGG ACTCTGAAGA

TGTACCTATG GTCCTAGTAG GAAATAAATG TGATTTGCCT TCTAGAACAG TAGACACAAA

ACAGGCTCAG GACTTAGCAA GAAGTTATGG AATTCCTTTT ATTGAAACAT CAGCAAAGAC

AAGACAGGTA AGTAACACTG AAATAAATAC AGATCTGTTT TCTGCAAAAT CATAACTGTT

ATGTCATTTA ATATATCAGT TTTTCTCTCA ATTATGCTAT ACTAGGAAAT AAAACAATAT
```

KRAS Ex5 NCBI Reference Sequence: NG_007524.1;
DNA; wildtype

SEQ ID NO. 200

AATGCAACAG ACTTTAAAGA AGTTGTGTTT TACAATGCAG AGAGTGGAGG ATGCTTTTTA

TACATTGGTG AGGGAGATCC GACAATACAG ATTGAAAAAA ATCAGCAAAG AAGAAAAGAC

TCCTGGCTGT GTGAAAATTA AAAAATGCAT TATAATGTAA TCTGGTAAGT TTAAGTTCAG

NRAS Exon 2 NCBI Reference Sequence: NG_007572.1;
DNA; wildtype

SEQ ID NO. 201

GTGTTTTTGC GTTCTCTAGT CACTTTAAGA ACCAAATGGA AGGTCACACT AGGGTTTTCA

TTTCCATTGA TTATAGAAAG CTTTAAAGTA CTGTAGATGT GGCTCGCCAA TTAACCCTGA

TTACTGGTTT CCAACAGGTT CTTGCTGGTG TGAAATGACT GAGTACAAAC TGGTGGTGGT

TGGAGCAGGT GGTGTTGGGA AAAGCGCACT GACAATCCAG CTAATCCAGA ACCACTTTGT

AGATGAATAT GATCCCACCA TAGAGGTGAG GCCCAGTGGT AGCCCGCTGA CCTGATCCTG

TCTCTCACTT GTCGGATCAT CTTTACCCAT ATTCTGTATT AAAGGAATAA GAGGAGAGAA

AGTAAAAAGT TATTTTGGGT ATACATTCAG TTATGCAATA AGCTTAACGT GTTTATAGAG

AACAGTTCAT TTTTATTAGC TGCTGAAGTT CTAAAACCT GTCCAGTTTT TAACAGTTCT

NRAS Exon 3 NCBI Reference Sequence: NG_007572.1;
DNA; wildtype

SEQ ID NO. 202

TGGGCTTGAA TAGTTAGATG CTTATTTAAC CTTGGCAATA GCATTGCATT CCCTGTGGTT

TTTAATAAAA ATTGAACTTC CCTCCCTCCC TGCCCCCTTA CCCTCACAC CCCCAGGATT

CTTACAGAAA ACAAGTGGTT ATAGATGGTG AAACCTGTTT GTTGGACATA CTGGATACAG

CTGGACAAGA AGAGTACAGT GCCATGAGAG ACCAATACAT GAGGACAGGC GAAGGCTTCC

TCTGTGTATT TGCCATCAAT AATAGCAAGT CATTTGCGGA TATTAACCTC TACAGGTACT

AGGAGCATTA TTTTCTCTGA AAGGATGATC TTTGTGTTCT GAATCTTTAT GGGGAAATGA

GGTTACCACA CTAGGGAAGA TAGAGCTTTT TAATTATGGG AAGAGTTGGT TTTAGGTTGT

TTGACATTGA GAATCTAGGG TAATTACTGA AAGTTAATAC TGGAATTTAT TTTACATAAT

NRAS Exon 4 NCBI Reference Sequence: NG_007572.1;
DNA; wildtype

SEQ ID NO. 203

TGGATACAGC TGGACAAGAA GAGTACAGTG CCATGAGAGA CCAATACATG AGGACAGGCG

AAGGCTTCCT CTGTGTATTT GCCATCAATA ATAGCAAGTC ATTTGCGGAT ATTAACCTCT

ACAGGGAGCA GATTAAGCGA GTAAAAGACT CGGATGATGT ACCTATGGTG CTAGTGGGAA

ACAAGTGTGA TTTGCCAACA AGGACAGTTG ATACAAAACA AGCCCACGAA CTGGCCAAGA

GTTACGGGAT TCCATTCATT GAAACCTCAG CCAAGACCAG ACAGGGTGTT GAAGATGCTT

TTTACACACTGGTAAGAGAA ATACGCCAGT ACCGAATGAA AAAACTCAAC AGCAGTGATG

ATGGGACTCA GGGTTGTATG GGATTGCCAT GTGTGGTGAT GTAACAAGAT ACTTTTAAAG

PIK3CA Ex9 NCBI Reference Sequence: NG_012113.2;
DNA; wildtype

SEQ ID NO. 204

TGTAAAATTT ATTGAAAATG TATTTGCTTT TTCTGTAAAT CATCTGTGAA TCCAGAGGGG

AAAAATATGA CAAAGAAAGC TATATAAGAT ATTATTTTAT TTTACAGAGT AACAGACTAG

CTAGAGACAA TGAATTAAGG GAAAATGACA AGAACAGCT CAAAGCAATT TCTACACGAG

ATCCTCTCTC TGAAATACACT GAGCAGGAGA AAGATTTTCT ATGGAGTCAC AGGTAAGTGC

TAAAATGGAG ATTCTCTGTT TCTTTTTCTT TATTACAGAA AAAATAACTG AATTTGGCTG

ATCTCAGCAT GTTTTTACCA TACCTATTGG AATAAATAAA GCAGAATTTA CATGATTTTT

PIK3CA Ex20NCBI Reference Sequence: NG_012113.2;
DNA; wildtype
SEQ ID NO. 205
TAGCTATTCG ACAGCATGCC AATCTCTTCA TAAATCTTTT CTCAATGATG CTTGGCTCTG

GAATGCCAGA ACTACAATCT TTTGATGACA TTGCATACAT TCGAAAGACC CTAGCCTTAG

ATAAAACTGA GCAAGAGGCT TTGGAGTATT TCATGAAACA AATGAATGAT GCACATCATG

GTGGCTGGAC AACAAAAATG GATTGGATCT TCCACACAAT TAAACAGCAT GCATTGAACT

GAAAAGATAA CTGAGAAAAT GAAAGCTCAC TCTGGATTCC ACACTGCACT GTTAATAACT

PIK3CA Ex16 NCBI Reference Sequence: NG_012113.2;
DNA; wildtype
SEQ ID NO. 206
GTTGTAAATCTTTGTAACACTTCAAAAAGCTATATTGTATTTATATTTTAAAATAAATTTCAGGGTAAA

ATAATAATAAAGCAAAGGTACCTAGTAAAGTTTTTAACTATTTTAAAGGCTTGAAGAGTGTCGAATTA

TGTCCTCTGCAAAAAGGCCACTGTGGTTGAATTGGGAGAACCCAGACATCATGTCAGAGTTACTGTTT

CAGAACAATGAGATCATCTTTAAAAATGGGGATGGTAAGGAAGAGTATTAATGAGCTTATGATGCATG

AATTTAGCTATCTTTTTATACACAGGATATTTATGAACCATGAAAACTACTGAAAGCCATTTAAGGAAT

ATACACATGTGATAAAATATGTAATATTTATCAGATGTCTTGACCTTTGAAATATGCATGTATAATCAA

TGAAAAGAAAAGAAGTACTAGGTTTAGATCAGAAGTCCTGAAATCAGTTTTTTGTTTTTTCTTTTTCCT

GTTCCCTGCC

All literature and similar materials cited in this application including, but not limited to, patents, patent applications, articles, books, treatises, and internet web pages, regardless of the format of such literature and similar materials, are expressly incorporated by reference in their entirety for any purpose as if they were entirely denoted. In the event that one or more of the incorporated literature and similar materials defines or uses a term in such a way that it contradicts that term's definition in this application, this application controls.

Although the foregoing description contains many specifics, these should not be construed as limiting the scope of the present invention, but merely as providing illustrations of some of the presently preferred embodiments. Similarly, other embodiments may be devised without departing from the spirit or scope of the present invention. Features from different embodiments may be employed in combination. The scope of the invention is, therefore, indicated and limited only by the appended claims and their legal equivalents rather than by the foregoing description. All additions, deletions and modifications to the invention as disclosed herein which fall within the meaning and scope of the claims are to be embraced thereby.

What is claimed is:

1. A method for enriching a target polynucleotide sequence containing a genetic variation, said method comprising:
   (a) providing a biological sample;
   (b) isolating DNA from said biological sample; said DNA including said target polynucleotide sequence containing a genetic variation;
   (c) providing two primer probes targeted to said target polynucleotide sequence said primer probes allowing formation of a PCR process product;
   (d) providing a target specific xenonucleic acid clamp oligomer probe specific for a wildtype polynucleotide sequence; having SEQ ID NO: 188; wherein said target specific xenonucleic acid clamp provides a Tm differential of about 15°-20° C. so that during the qPCR process only mutant templates are amplified;
   (e) admixing the primer probes and the xenonucleic clamping probe with the target nucleic acid sample;
   (f) performing a PCR amplification process in a reaction solution under hybridization conditions thereby generating multiple amplicons; and
   (g) detecting said amplicons.

2. The method of claim 1, wherein said detection employs oligonucleotide probes specific for hybridization of variant polynucleotide amplicon sequences.

3. The method of claim 1, wherein the target polynucleotide sequence containing a genetic variation is in a gene selected from the group consisting of: KRAS, BRAF, EGFR, TP53, JAK2, NPM1, and PCA3.

4. A method for enriching multiple target polynucleotide sequences containing a genetic variation said method comprising:
   (a) providing a biological sample;
   (b) isolating DNA from said biological sample; said DNA including said multiple target polynucleotide sequences containing a genetic variation;
   (c) providing a library of amplifying primer probes targeted to said multiple target polynucleotide sequences containing a genetic variation; said primer probes allowing formation of PCR process products;
   (d) providing a library of target specific xenonucleic acid clamp oligomer probes specific for multiple wildtype polynucleotide sequences selected from the group consisting from SEQ ID NO: 187 to SEQ ID NO: 189; wherein said target specific xenonucleic acid clamps provides a Tm differential of about 15°-20° C. so that during the qPCR process only mutant templates are amplified;
   (e) admixing the primer probes and the xenonucleic clamping probes with the multiple target nucleic add samples;
   (f) performing a PCR amplification process in a reaction solution under hybridization conditions thereby generating multiple amplicons; and
   (g) detecting said amplicons.

5. The method of claim 3, wherein said detection employs oligonucleotide probes specific for hybridization of variant polynucleotide amplicon sequences.

6. A method for conducting a minimally invasive biopsy in a mammalian subject suspected of a having a neoplastic disease, said method comprising:
   (a) providing a biological sample derived from said mammalian subject;
   (b) isolating DNA from said biological sample; said DNA including multiple target polynucleotide sequences containing a genetic variation;

(c) providing a library of amplifying primer probes targeted to said multiple target poly-nucleotide sequences containing a genetic variation; said primer probes allowing formation of PCR process products;
(d) providing a library of target specific xenonucleic acid clamp oligomer probes specific for multiple wildtype polynucleotide sequences selected from the group consisting from SEQ ID SEQ ID NO: 187 to SEQ ID NO: 189; wherein said target specific xenonucleic acid clamps provides a Tm differential of about 15°-20° C. so that during the qPCR process only mutant templates are amplified;
(e) admixing the primer probes and the xenonucleic clamping probes with the multiple target nucleic acid samples;
(f) performing a PCR amplification process in a reaction solution under hybridization conditions thereby generating multiple amplicons; and
(f) detecting said amplicons.

7. The method of claim 5, wherein said biological sample are cells derived from said mammalian subject.

8. The method of claim 5, wherein said target polynucleotides containing a genetic variation are derived from free circulating cell free polynucleotides derived from said mammalian subject.

9. The method of claim 4, which includes using multiple Xenonucleic acid clamp probes and amplifying primers targeted to multiple polynucleotide sequences.

* * * * *